United States Patent
Sato et al.

(10) Patent No.: US 10,786,603 B2
(45) Date of Patent: Sep. 29, 2020

(54) MULTILAYER SHEET, INTEGRATED SHEET USING SAME, AND MANUFACTURING METHOD THEREFOR

(71) Applicant: Toray Industries, Inc., Tokyo (JP)

(72) Inventors: Teruhisa Sato, Otsu (JP); Yoshikazu Yakake, Otsu (JP); Toru Arakane, Urayasu (JP); Ai Suzuki, Otsu (JP)

(73) Assignee: Toray Industries, Inc., Tokyo (JP)

( * ) Notice: Subject to any disclaimer, the term of this patent is extended or adjusted under 35 U.S.C. 154(b) by 126 days.

(21) Appl. No.: 15/300,343

(22) PCT Filed: Mar. 31, 2015

(86) PCT No.: PCT/JP2015/060056
§ 371 (c)(1),
(2) Date: Sep. 29, 2016

(87) PCT Pub. No.: WO2015/152204
PCT Pub. Date: Oct. 8, 2015

(65) Prior Publication Data
US 2017/0136157 A1    May 18, 2017

(30) Foreign Application Priority Data
Mar. 31, 2014    (JP) .................. 2014-072603

(51) Int. Cl.
*A61L 31/14*    (2006.01)
*A61L 31/10*    (2006.01)
(Continued)

(52) U.S. Cl.
CPC ............. *A61L 31/14* (2013.01); *A61L 31/041* (2013.01); *A61L 31/10* (2013.01); *B32B 3/26* (2013.01);
(Continued)

(58) Field of Classification Search
CPC ........ A61L 31/14; A61L 31/041; A61L 31/10; A61L 2420/08; B32B 7/02; B32B 3/263;
(Continued)

(56) References Cited

U.S. PATENT DOCUMENTS 5,567,510 A * 10/1996 Patnode .................. A61L 15/62
428/903
5,630,972 A * 5/1997 Patnode .................. A61L 15/62
264/103
(Continued)

FOREIGN PATENT DOCUMENTS

EP    3 159 444    4/1917
EP    2 377 680    10/2011
(Continued)

OTHER PUBLICATIONS

The First Office Action dated Nov. 17, 2017, of corresponding Chinese Application No. 201580018096.7, along with an English translation.
(Continued)

*Primary Examiner* — Michael Zhang
(74) *Attorney, Agent, or Firm* — DLA Piper LLP (US)

(57) ABSTRACT

A multilayer sheet can be used in vivo or in an environment in which moisture is adhered, an integrated sheet including the multilayer sheet and a base material, and methods for producing the same. The multilayer sheet has one or more layers from each of a layer (A) composed of sparingly water-soluble polymer and a fiber layer (B) composed of water-soluble polymer are laminated, and at least one of outermost layers is the above-described layer (A) composed of sparingly water-soluble polymer. The time taken from dropping of water onto a surface of the outermost layer of
(Continued)

the above-described layer (A) composed of sparingly water-soluble polymer to dissolution of the other outermost layer is 10 seconds to 5 minutes.

4 Claims, 6 Drawing Sheets

(51) Int. Cl.
| | | |
|---|---|---|
| *B32B 5/26* | (2006.01) | |
| *B32B 3/26* | (2006.01) | |
| *B32B 7/02* | (2019.01) | |
| *A61L 31/04* | (2006.01) | |
| *B32B 5/02* | (2006.01) | |
| *B32B 27/36* | (2006.01) | |
| *D01D 5/00* | (2006.01) | |

(52) U.S. Cl.
CPC ............ *B32B 3/263* (2013.01); *B32B 5/022* (2013.01); *B32B 5/26* (2013.01); *B32B 7/02* (2013.01); *B32B 27/36* (2013.01); *A61L 2420/08* (2013.01); *B32B 2262/0223* (2013.01); *B32B 2262/04* (2013.01); *B32B 2307/54* (2013.01); *B32B 2307/718* (2013.01); *B32B 2307/7166* (2013.01); *B32B 2556/00* (2013.01); *D01D 5/003* (2013.01)

(58) Field of Classification Search
CPC .. B32B 3/26; B32B 5/26; B32B 27/36; B32B 5/022; B32B 2262/04; B32B 2262/0223; B32B 2556/00; B32B 2307/7166; B32B 2307/54; B32B 2307/718; D01D 5/003
See application file for complete search history.

(56) References Cited

U.S. PATENT DOCUMENTS

| | | |
|---|---|---|
| 2003/0100955 A1 | 5/2003 | Greenawalt et al. |
| 2008/0254091 A1 | 10/2008 | Lee et al. |
| 2009/0291282 A1* | 11/2009 | Kitamura ............... C08J 5/18 428/220 |
| 2012/0095418 A1* | 4/2012 | Stopek ............. A61K 9/7007 604/304 |
| 2012/0301515 A1 | 11/2012 | Tani et al. |
| 2013/0122069 A1* | 5/2013 | Tojo ................. A61K 8/0208 424/401 |
| 2013/0142852 A1* | 6/2013 | Tojo ................. A61K 8/0208 424/401 |
| 2015/0209243 A1* | 7/2015 | Shiroya ............. A61K 8/676 424/401 |
| 2015/0265030 A1* | 9/2015 | Kusukame ......... A45D 44/002 132/200 |
| 2015/0282595 A1* | 10/2015 | Kimura ............. A61Q 17/04 132/200 |

FOREIGN PATENT DOCUMENTS

| | | |
|---|---|---|
| JP | 57-167919 A | 10/1982 |
| JP | 2003-516816 A | 5/2003 |
| JP | 2003-518167 A | 6/2003 |
| JP | 2009-506861 A | 2/2009 |
| JP | 5143396 B2 | 2/2013 |
| WO | 01/46265 A1 | 6/2001 |
| WO | 2007/109353 | 9/2007 |
| WO | 2011/081162 A1 | 7/2011 |
| WO | 2012/002390 A1 | 1/2012 |

OTHER PUBLICATIONS

Supplementary European Search Report dated Oct. 17, 2017, of corresponding European Application No. 15774082.0.

Examination Report dated Oct. 23, 2019, of corresponding Indian Application No. 201647032133.

* cited by examiner

MULTILAYER SHEET, INTEGRATED SHEET USING SAME, AND MANUFACTURING METHOD THEREFOR

TECHNICAL FIELD

This disclosure relates to a multilayer sheet composed of at least two or more polymer layers mainly used in vivo or in an environment in which moisture is adhered, and suitably used as a backing for an anti-adhesion material or the like, an integrated sheet using the multilayer sheet, and a method of producing the multilayer sheet.

BACKGROUND

When normal tissues injured by surgery are sutured together, the tissues connect and heal naturally. However, tissues originally separate from one another may connect in the course of healing, leading to a so-called post-operative adhesion. In laparotomy, such post-operative adhesions are said to occur at a probability of 90% or higher, including adhesions that are not clinically problematic and, therefore, various measures have been made for the purpose of preventing adhesions.

For example, to reduce adhesion formation, the use of a water-soluble anti-adhesion material such as an aqueous solution of sodium alginate or an aqueous solution of sodium hyaluronate has been proposed (JP Patent Publication (Kokai) No. 57-167919 A (1982)). However, although the anti-adhesion material described in JP '919 is effective to some extent, because it is water-soluble, the anti-adhesion material has not only the possibility of flowing out into portions other than the site requiring adhesion prevention, without remaining in its required place, but also has even the possibility of causing adhesions of normal sites.

A method of preventing adhesions of tissues by providing physical barriers on injured tissues is therefore known. Examples of such physical barriers include polypropylene resins, silicone resins, and polytetrafluoroethylene resins. While these materials (resins) can function sufficiently as barriers, they have the problem of having relatively low bioactivity, and remaining in vivo without being absorbed.

To solve this problem, an anti-adhesion material in which a natural polymer is used as a bioabsorbable material has been developed. Specifically, an anti-adhesion material composed of sodium hyaluronate and carboxymethylcellulose has been proposed (see JP Patent Publication (Kohyo) No. 2003-518167 A). The raw materials used in that proposal, however, have high water absorbency and, therefore, have the problem of adhering due to moisture adhered to surgical tools or moisture in an organ other than the tissues of the affected site and, thus, are disadvantageous in terms of operability. Additionally, an anti-adhesion material with a three-layer structure has been considered and proposed, in which a hydrophilic polysaccharide is used to allow adhesiveness to be expressed when the surface is wet so that the anti-adhesion material has excellent biocompatibility, and satisfactory strength when wet, and crack resistance when bent (see JP Patent No. 5143396). In that proposal, however, similarly, the anti-adhesion material has the problem of being sticky when wet before being adhered to tissues.

Moreover, to deal with wetting, an anti-adhesion material has been proposed in which the surface of a polysaccharide is coated with an aliphatic ester so that the anti-adhesion material does not become sticky when wet (International Publication No. WO 11/081162). All of such anti-adhesion materials, however, are in the form of films and, thus, are poor in flexibility and are disadvantageous in terms of operability compared to knits or nonwoven fabrics.

An anti-adhesion material in which oxidized cellulose is used is also known. However, when that anti-adhesion material is used in the presence of blood as a sponge or knit composed of oxidized cellulose, the anti-adhesion material has no hemostatic effect, and may promote adhesions, even though it has excellent flexibility and operability.

On the other hand, an anti-adhesion material with a multilayer structure including a hydrophobic nanofibrous-structured base material layer and a hydrophilic polymer layer has been proposed (JP Patent Publication (Kohyo) No. 2009-506861 A). However, although the anti-adhesion material described in JP '861 has excellent flexibility and excellent operability owing to its nanofibrous structure, because the hydrophobic base material layer has a fibrous structure and thus, has satisfactory water permeability, adhesion of moisture to any of the layers causes the hydrophilic polymer layer to dissolve and adhere, thus leading to the problem of poor handleability.

As a technique to solve the problems due to wetting as seen in the conventional anti-adhesion materials, it may be effective to integrate a biodegradable and bioabsorbable base material having a hemostatic effect and an anti-adhesion effect, and a backing that compensates for strength or the like insufficient in the base material to improve operability. As described above, however, a sufficient effect has not been obtained with the conventional techniques.

As described above, the anti-adhesion materials currently in use or under consideration have poor operability, or are restricted in use in the presence of moisture or blood. It could therefore be helpful to provide an anti-adhesion material in which the problems associated with operability, strength, and the like due to wetting as seen in the conventional anti-adhesion materials have been solved.

SUMMARY

We integrate a biodegradable and bioabsorbable base material having poor operability or subject to restrictions on use in the presence of moisture or blood, and as a backing, a multilayer sheet satisfies the following requirements (1) to (3):

(1) A certain time is taken from adhesion of moisture to the surface of an outermost layer of the multilayer sheet to dissolution of the other outermost layer.

(2) When the multilayer sheet and the base material are integrated, operability similar to that of a knit or nonwoven fabric can be provided.

(3) After the multilayer sheet and the base material are integrated, and then the surface of the base material is affixed to tissues as an anti-adhesion material, for example, the multilayer sheet is quickly removed.

As a result, we found that a multilayer sheet is obtained by providing a multilayer sheet in which at least one or more layers from each of a layer (A) composed of sparingly water-soluble polymer, of which solubility has been controlled, and a fiber layer (B) composed of water-soluble polymer are laminated, and at least one of outermost layers is the layer (A) composed of sparingly water-soluble polymer.

The thickness of the above-described layer (A) composed of sparingly water-soluble polymer is preferably 0.1 to 1,000 μm, and the thickness of the above-described fiber layer (B) composed of water-soluble polymer is preferably 10 to 10,000 μm.

Preferably, the above-described fiber layer (B) composed of water-soluble polymer has a fiber diameter of 0.001 to 100 μm.

In the multilayer sheet, the above-described layer (A) composed of sparingly water-soluble polymer preferably has a film structure composed of the sparingly water-soluble polymer in at least a portion thereof.

Preferably, the sparingly water-soluble polymer forming the above-described layer (A) composed of sparingly water-soluble polymer has a solubility in water at a temperature of 95° C. that is not less than 10 times its solubility in water at a temperature of 20° C.

Preferably, the compound forming the above-described fiber layer (B) composed of water-soluble polymer is selected from partially saponified polyvinyl alcohols, modified polyvinyl alcohols to which functional groups have been introduced by copolymerization, terminal modification, and a subsequent reaction, pullulan, hyaluronic acid, alginic acid, and any combination thereof.

We also found that the above-described multilayer sheet is obtained using a production method that satisfies the following requirements (1) to (5):

(1) A polymer solution is formed by dissolving a polymer in a solvent at least partially containing water or an organic solvent.
(2) A portion of the solvent is evaporated during the formation of a layer using the above-described polymer solution as a raw material.
(3) A fiber layer (B) composed of water-soluble polymer is formed, and then a layer (A) composed of sparingly water-soluble polymer is laminated on the fiber layer (B).
(4) When the above-described layer (A) composed of sparingly water-soluble polymer is formed on the above-described fiber layer (B) composed of water-soluble polymer, the above-described fiber layer (B) composed of water-soluble polymer is partially dissolved.
(5) The above-described layer (A) composed of sparingly water-soluble polymer is laminated to form an outermost layer.

In the method of producing a multilayer sheet, preferably, the layer (A) composed of sparingly water-soluble polymer is formed on the fiber layer (B) composed of water-soluble polymer, using an electrospinning method.

Preferably, during formation of the layer (A) composed of sparingly water-soluble polymer using the electrospinning method, a distance between a nozzle tip and a collection electrode is set at 3 to 10 cm.

We thus provide:

(1) A multilayer sheet wherein:
one or more layers from each of
a layer (A) composed of sparingly water-soluble polymer and
a fiber layer (B) composed of water-soluble polymer are laminated, and
at least one of outermost layers is the layer (A) composed of sparingly water-soluble polymer; and
time taken from dropping of water onto a surface of the outermost layer of the layer (A) composed of sparingly water-soluble polymer to dissolution of the other outermost layer is 10 seconds to 5 minutes.
(2) The multilayer sheet according to (1), wherein the layer (A) composed of sparingly water-soluble polymer has a thin-film structure partially having a defect or having an uneven thickness.
(3) The multilayer sheet according to (1) or (2), wherein a basis weight of the layer (A) composed of sparingly water-soluble polymer is 1 to 200 g/m².
(4) The multilayer sheet according to any of (1) to (3), wherein
the compound forming the layer (A) composed of sparingly water-soluble polymer is selected from the group consisting of a highly saponified polyvinyl alcohol, a fully saponified polyvinyl alcohol, carboxymethylcellulose, methylcellulose, hydroxypropyl cellulose, hydroxymethylcellulose, and any combination thereof
(5) The multilayer sheet according to any of (1) to (4), wherein the multilayer sheet has a tensile strength of 0.1 to 5.0 N/mm.
(6) The multilayer sheet according to any of (1) to (5), wherein
the layer (A) composed of sparingly water-soluble polymer is formed by collecting a fiber obtained by spinning a solution of the compound forming the layer using an electrospinning method, onto the fiber layer (B) composed of water-soluble polymer, and the spinning is performed by setting a distance between a nozzle tip that discharges the solution and a collection electrode to be 3 to 10 cm.
(7) An integrated sheet wherein:
a multilayer sheet according to any of (1) to (6) and
a base material (C) composed of a sparingly water-soluble polymer
are integrally laminated, and
the layer (A) composed of sparingly water-soluble polymer forms one outermost layer, and the base material (C) composed of sparingly water-soluble polymer forms the other outermost layer.
(8) A method of producing a multilayer sheet comprising:
a first step of forming a fiber layer (B) composed of water-soluble polymer by collecting a fiber obtained by spinning a solution of a water-soluble polymer; and
a second step of forming a layer (A) composed of sparingly water-soluble polymer by collecting a fiber obtained by spinning a solution of a sparingly water-soluble polymer, onto the fiber layer (B) composed of water-soluble polymer, wherein
in the second step, the fiber layer (B) composed of water-soluble polymer is partially dissolved when the fiber obtained by spinning the solution of the sparingly water-soluble polymer is collected.
(9) The method of producing a multilayer sheet according to (8), wherein, in the second step, the spinning is performed using an electrospinning method.
(10) The method of producing a multilayer sheet according to (9), wherein the spinning is performed by setting a distance between a nozzle tip that discharges the solution and a collection electrode to be 3 to 10 cm.

A multilayer sheet composed of at least the layer (A) composed of sparingly water-soluble polymer and the fiber layer (B) composed of water-soluble polymer is obtained, and this multilayer sheet is laminated and integrated with a biodegradable and bioabsorbable base material, thus obtaining an integrated sheet.

Because the multilayer sheet is composed of at least the layer (A) composed of sparingly water-soluble polymer and the fiber layer (B) composed of water-soluble polymer, it has two aspects of solubility in water, as well as flexibility and shape-memory properties. This allows the handleability of the integrated base material when the multilayer sheet is used as a backing of the biodegradable and bioabsorbable base material. Furthermore, because the multilayer sheet shows a certain degree of water resistance against the adhesion of moisture to the layer (A) composed of sparingly water-soluble polymer as an outermost layer, the multilayer sheet can be used in vivo or in an environment in which moisture is adhered, and because the other outermost layer is dissolved after a lapse of a certain time, the multilayer sheet when integrated can be removed from the base material. The multilayer sheet, therefore, can be suitably used as a backing of an anti-adhesion material in which a certain degree of water resistance and handleability are required.

This application claims priority of the contents of the specification, claims, and drawings of JP Patent Application No. 2014-072603.

Figure 1:
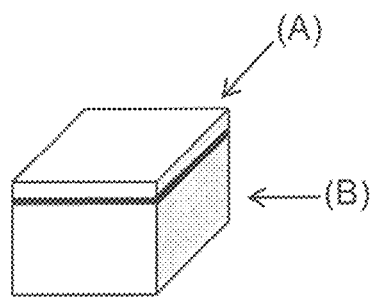
FIG. 1 shows a perspective view showing one exemplary structure of a multilayer sheet.

REFERENCE NUMERALS (A): layer including a sparingly water-soluble polymer
(B): fiber layer including a water-soluble polymer
(C): base material including a sparingly water-soluble polymer

DETAILED DESCRIPTION

The multilayer sheet is at least one or more layers from each of a layer (A) composed of sparingly water-soluble polymer and a fiber layer (B) composed of water-soluble polymer are laminated, and at least one of outermost layers is the above-described layer (A) composed of sparingly water-soluble polymer, wherein time taken from dropping of water onto a surface of the above-described layer (A) composed of sparingly water-soluble polymer as the outermost layer to dissolution of the other outermost layer is 10 seconds to 5 minutes.

The above-described time is measured based on a method similar to the dropping method according to JIS L 1907 (2010). Specifically, as in the dropping method according to JIS L 1907 (2010), the height from the surface of a specimen to the tip of a burette is adjusted to 10 mm. The start time is defined as the time when one droplet (approximately 0.04 ml) of water dropped from the burette has reached the surface of the outermost layer (A) of the specimen, and the end time is defined as the time when the water after penetrating through the outermost layer (A), a lower layer thereof, and then the other outermost layer as the lowermost layer has dissolved the other outermost layer. Then, the time taken from the start time to the end time is measured. The term "dissolved" means the state where 20% of the polymer forming the layer is dissolved into water, or the state where the polymer has collapsed without being able to maintain its layer shape. Whether the polymer is dissolved or not is determined through visual observation from various directions such as the outermost layer (A) side and a cross section side. The expression "20% of the polymer forming the layer is dissolved into water" means that in the above-described measurement of the dissolution time, the color of the specimen in a portion where the water has penetrated through to the outermost layer changes from white to transparent, and therefore, after one droplet of water is dropped from the burette, the water drop is observed directly from above the specimen, and the proportion of the area of the portion where the color has changed to transparent, relative to the area of the circle of the water drop, reaches 20%.

Preferably, a portion of the above-described layer (A) composed of sparingly water-soluble polymer is composed of a discontinuous film or a layered film partially having a defect portion, which has a nano-order or submicron-order thickness.

Preferably, the basis weight of the above-described layer (A) composed of sparingly water-soluble polymer is 1 to 200 g/m$^2$, and the basis weight of the above-described fiber layer (B) composed of water-soluble polymer is 5 to 500 g/m$^2$.

Preferably, the compound forming the above-described layer (A) composed of sparingly water-soluble polymer is selected from the group consisting of a highly saponified polyvinyl alcohol, a fully saponified polyvinyl alcohol, carboxymethylcellulose, methylcellulose, hydroxypropylcellulose, hydroxymethylcellulose, and any combination thereof.

Preferably, the multilayer sheet has a tensile strength of 0.1 to 5.0 N/mm.

Furthermore, in the integrated sheet, the above-described multilayer sheet and a base material (C) composed of sparingly water-soluble polymer are integrally laminated, and the above-described layer (A) composed of sparingly water-soluble polymer forms one outermost layer, and the above-described base material (C) composed of sparingly water-soluble polymer forms the other outermost layer.

As described above, in the multilayer sheet, a certain time is taken from adhesion of moisture to the layer (A) composed of sparingly water-soluble polymer as the outermost layer described above to dissolution of the other outermost layer. Therefore, when the above-described multilayer sheet is used as a backing, and the base material (C) composed of sparingly water-soluble polymer is integrally laminated thereto to form an integrated sheet in which each of the above-described layer (A) composed of sparingly water-soluble polymer and the above-described base material (C) composed of sparingly water-soluble polymer is formed as an outermost layer, properties similar to those of a knit or nonwoven fabric can be imparted to the base material, thus leading to improved handleability. Furthermore, because the fiber layer (B) composed of water-soluble polymer is provided in the integrated sheet, after the surface having the base material (C) of the integrated sheet is affixed to wound tissues as an anti-adhesion material, for example, the multilayer sheet as the backing can be quickly removed.

Examples of functionalities required in the multilayer sheet as the backing include: (1) having a certain basis weight to impart a feeling of holding similar to that when holding gauze to the integrated anti-adhesion material; (2) having flexibility to not prevent the integrated anti-adhesion material from being rolled up to a small size, or to not prevent the anti-adhesion material from conforming to tissues; (3) having shape-memory properties to allow the rolled-up anti-adhesion material to be spread and restored; (4) having a certain strength such that the anti-adhesion material is not broken when a jig such as a trocar is used in laparoscopic surgery, or can be cut with scissors; (5) not dissolving in the moisture or blood with which the anti-adhesion material may be contacted during surgery to affix the integrated anti-adhesion material to target tissues; (6) having biocompatibility to avoid inflammation in vivo, and having excellent bioabsorbability and biodegradability or having an excellent ability of being excreted out of the body so that the removed backing does not become a hotbed of bacteria; and (7) allowing the backing to be readily removed from the integrated anti-adhesion material, to not inhibit the anti-adhesion material from stopping bleeding or preventing adhesions of tissues. The multilayer sheet preferably satisfies these requirements.

The sparingly water-soluble polymer forming the layer (A) composed of sparingly water-soluble polymer refers to a polymer having the following properties: when 1 g of the polymer at ordinary temperature (20° C.±5° C.) is weighed and immersed in 9 g of water in an environment at 1 atmospheric pressure, after a lapse of a sufficient time (at least 24 hours, for example), 80 mass % or more of the immersed polymer is not dissolved. The sparingly water-soluble polymer includes a polymer of which 20 mass % or more is dissolvable in water at a high temperature of 95° C. or higher, and of which 80 mass % or more does not precipitate as solids when slowly cooled to ordinary temperature.

Furthermore, the sparingly water-soluble polymer forming the layer (A) composed of sparingly water-soluble polymer, when prepared as an aqueous solution, preferably has a solubility in water at a temperature of 95° C. that is not less than 10 times its solubility in water at a temperature of 20° C. In this case, the formed layer (A) composed of sparingly water-soluble polymer is relatively likely to dissolve in water at high temperature, and is relatively unlikely to dissolve in water at ordinary temperature. In particular, preferably in the formation of the layer (A) composed of sparingly water-soluble polymer that, after the sparingly water-soluble polymer is dissolved in water at high temperature, it does not precipitate at ordinary temperature after being slowly cooled. Furthermore, it is preferred that as described below, the layer (A) of sparingly water-soluble polymer is a discontinuous film or a layered film partially having a defect portion because a balance of water permeability and water retention can thus be achieved for the multilayer sheet having the layer (A) composed of sparingly water-soluble polymer as the outermost layer.

Specific examples of the sparingly water-soluble polymer forming the layer (A) composed of sparingly water-soluble polymer include a highly saponified polyvinyl alcohol (hereinafter, a polyvinyl alcohol may be referred to as PVA), fully saponified PVA, an oxazoline-modified silicone such as a poly(N-propanoylethyleneimine) graft-dimethyl siloxane/γ-aminopropyl-methylsiloxane copolymer, zein (a principal component of corn protein), synthetic polymers such as polyester, polylactic acid, polyacrylonitrile, polymethacrylic acid, polystyrene, polyvinyl butyral, polyethylene terephthalate, polybutylene terephthalate, polyurethane, polyamide, polyimide, and polyamide-imide, semi-synthetic polymers including celluloses such as carboxymethylcellulose, methylcellulose, hydroxypropylcellulose, and hydroxymethylcellulose, polysaccharides such as amylose, amylopectin, and starch as a mixture thereof, xylans such as arabinoxylan and glucuronoxylan, pectic polysaccharides such as galactans, xyloglucans, mannan such as glucomannan, mucopolysaccharides such as chondroitin and glucosamine, an animal polysaccharide such as glycogen, and a natural polymer such as gellan gum.

These sparingly water-soluble polymers can be used singly, or in combinations of two or more. Among the above-described various water-soluble polymers, highly saponified PVA and fully saponified PVA are preferably used, because, when preparing aqueous solutions, they have a particularly high solubility in water at a temperature of 95° C., compared to their solubility in water at a temperature of 20° C.

Furthermore, the sparingly water-soluble polymer preferably has biocompatibility so that when the multilayer sheet is formed and used as a backing of an anti-adhesion material, it is absorbed in vivo even if the multilayer sheet is left without being removed, or it is excreted through physiological action. PVA and celluloses, which have been known for long as biocompatible materials, are preferably used, because the solubility and the aqueous solution viscosity thereof can be adjusted by controlling the degree of saponification, degree of esterification, and degree of polymerization, and because they have general versatility. A material having "biocompatibility" refers to a material having little or no stimulation or adverse effects upon living tissues. More specifically, the material means one which does not cause generation or elution of a substance hazardous to living tissues, and one such that living tissues contacted with the material do not judge the material as a foreign substance and show defense reactions such as inflammation and blood coagulation.

PVA used in the layer (A) composed of sparingly water-soluble polymer is obtained by saponifying a polymer mainly having a vinyl ester unit. Examples of vinyl compound monomers for forming the vinyl ester unit include vinyl formate, vinyl acetate, vinyl propionate, vinyl valerate, vinyl caprate, vinyl laurate, vinyl stearate, vinyl benzoate, vinyl pivalate, and vinyl versatate. Among the above, vinyl acetate is preferably used in view of readily obtaining PVA.

PVA used in the layer (A) composed of sparingly water-soluble polymer preferably has a degree of saponification of 92.5 to 100 mol %. When PVA has a degree of saponification of at least 40 mol % or more, it has satisfactory thermal stability, and is unlikely to undergo pyrolysis or gelation. Thus, melt spinning is also possible. Furthermore, the higher degree of saponification described above is more preferred because the polymer forming the layer (A) composed of sparingly water-soluble polymer is unlikely to dissolve in water at ordinary temperature. In particular, PVA having a degree of saponification of less than 99.99 mol % shows no decrease in solubility, and enables more stable melt spinning, and therefore, the degree of saponification is more preferably 95 to 99.99 mol %, and a degree of saponification of 98 to 99.98 mol % is particularly preferred.

PVA used in the layer (A) composed of sparingly water-soluble polymer preferably has a degree of polymerization of 150 to 10,000. Where the degree of polymerization is within this range, when prepared as an aqueous solution, PVA has sufficient solubility in water, and has satisfactory moldability after the evaporation of water.

In the multilayer sheet, PVA more preferably has a degree of polymerization of 300 or more, and still more preferably 500 or more to impart water resistance to the layer (A) composed of sparingly water-soluble polymer, and improve the moldability after the evaporation of water. Furthermore, PVA more preferably has a degree of polymerization of 4,000 or less, and still more preferably 1,500 or less because PVA having a high degree of polymerization is unlikely to be degraded, absorbed, metabolized, or excreted in vivo, and when PVA having a high degree of polymerization is prepared as an aqueous solution, the viscosity thereof increases, and the efficiency of forming the layer deteriorates.

PVA described above or a sparingly water-soluble polymer having similar characteristics is unlikely to dissolve in water at ordinary temperature, but dissolves in hot water at a temperature of 95° C. or higher, and after being slowly cooled to ordinary temperature or lower, it does not precipitate if it is dissolved in an amount not greater than its saturation solubility, and thus, forms a uniform aqueous solution.

Preferably, the layer (A) composed of sparingly water-soluble polymer has a film structure composed of the sparingly water-soluble polymer in at least a portion thereof. It is preferred that the layer (A) composed of sparingly water-soluble polymer is a film having an uneven thickness, or a layered film partially having a defect, which has a nano-order or submicron-order thickness. With this structure being formed, when the blood or moisture is adhered to the surface of the layer (A) composed of sparingly water-soluble polymer, the sparingly water-soluble polymer forming the layer (A) composed of sparingly water-soluble polymer is not immediately dissolved, while the film having an uneven thickness or the film partially having a defect, which has a nano-order or submicron-order thickness, allows passage of water therethrough after a lapse of a certain time, though not immediately, which is preferable.

The number of laminated layers is not particularly limited so long as the layer (A) composed of sparingly water-soluble polymer does not become excessively thick to impair the texture of the multilayer sheet. Moreover, when a plurality of layers are formed, the layers may be formed into a single layer through fusion or welding of upper and lower layers. The number of the plurality of layers is preferably from several (2 to 3 layers) to 20,000, in view of satisfying both water resistance and texture. From the viewpoint of uniformly forming the film on the layer (A) composed of sparingly water-soluble polymer, the number of the layers is more preferably 20 or more, and still more preferably 100 or more. Furthermore, from the viewpoint of retaining satisfactory flexibility of the multilayer sheet, the number of the layers is preferably 5,000 or less, and still more preferably 1,000 or less. Note, however, that the plurality of layers may be formed into a single layer, as described above. This structure can impart an effect of making moisture adhered to the surface unlikely to dissolve the layer (A) composed of sparingly water-soluble polymer, or an effect of making the moisture unlikely to pass therethrough, and can prevent the texture of the layer (A) composed of sparingly water-soluble polymer from becoming excessively hardened. While the layer (A) composed of sparingly water-soluble polymer may be a uniform complete film, it preferably does not impair the flexibility of the entire multilayer sheet.

Moreover, in the multilayer sheet, the layer (A) composed of sparingly water-soluble polymer may be composed of a fibrous structure instead of the film structure. In this case, preferably, a film composed of a sparingly water-soluble polymer is at least partially formed by the layer (A) composed of sparingly water-soluble polymer or a layer other than the fiber layer (B) composed of water-soluble polymer. An example thereof may be a structure having the layer (A) composed of sparingly water-soluble polymer as an outermost layer, the film composed of the sparingly water-soluble polymer as an inner layer thereof, and the fiber layer (B) composed of water-soluble polymer as an inner layer thereof. Alternatively, in a multilayer sheet having a two-layer structure of the layer (A) composed of sparingly water-soluble polymer and the fiber layer (B) composed of water-soluble polymer, the layer (A) composed of sparingly water-soluble polymer preferably has a dense fibrous structure that does not readily allow passage of water. Furthermore, a film may be incorporated into a portion of the layer (A) composed of sparingly water-soluble polymer having a fibrous structure. A method of incorporating the film will be described in one exemplary method of producing a multilayer sheet described below.

Where the layer (A) composed of sparingly water-soluble polymer includes a fiber, the fiber may be either a long fiber or a short fiber, and the single fiber diameter is preferably smaller to such an extent that it does not interfere with spinning, from the viewpoint of obtaining a dense fibrous structure.

As used herein, the water-soluble polymer forming the fiber layer (B) composed of water-soluble polymer has the following properties: when 1 g of the polymer at ordinary temperature (20° C.±5° C.) is weighed and immersed in 9 g of water in an environment at 1 atmospheric pressure, after a lapse of a sufficient time (at least 24 hours, for example), 50 mass % or more of the immersed polymer is dissolved.

Examples of the water-soluble polymer forming the fiber layer (B) composed of water-soluble polymer include low-saponified PVA, partially saponified PVA, modified PVA to which functional groups have been introduced by copolymerization, terminal modification, and a subsequent reaction, polyethylene oxide, polyvinyl pyrrolidone, a butenediol-vinyl alcohol copolymer resin, sodium polyacrylate, thermoplastic starch, starch derivatives, polyhydroxyalkanoates, polyester amide, specific polyesters, a vinyl pyrrolidone-vinyl acetate copolymer, a styrene-vinyl pyrrolidone copolymer, a styrene-maleic anhydride copolymer, water-soluble polyester, water-soluble polyurethane, water-soluble nylon, a water-soluble epoxy resin, and other synthetic polymers, pullulan, hyaluronic acid, chondroitin sulfate, poly-γ-glutamic acid, modified cornstarch, β-glucan, glucooligosaccharide, heparin, keratosulfate, and other mucopolysaccharides, cellulose, pectin, xylan, lignin, glucomannan, galacturonic acid, psyllium seed gum, tamarind seed gum, gum arabic, tragacanth gum, water-soluble soybean polysaccharide, alginic acid, carrageenan, laminaran, agarose, fucoidan, and other natural polymers.

These water-soluble polymers can be used singly, or in combinations of two or more. Among the above-described various water-soluble polymers, a partially saponified polyvinyl alcohol, a modified polyvinyl alcohol, pullulan, hyaluronic acid, and alginic acid are preferably used, because they are satisfactory in spinnability and are biocompatible and, in particular, pullulan is preferably used.

As pullulan, pullulan produced by culturing a yeast of the genus *Aureobasidium* or the like in a medium containing a starch decomposition product is advantageously used, because it is usually advantageous in terms of availability and cost. For example, pullulan sold by Hayashibara Co., Ltd. (trade names "Pullulan PI-20," "Pullulan PF-20," and the like) can be suitably used. Other pullulan products can also be used without departing from the desired effects. Moreover, where necessary, pullulan containing, as a repeating unit, maltotriose derivatized by modification such as esterification with a given degree of substitution can also be used.

The weight average molecular weight of pullulan is preferably 5,000 to 1,000,000 daltons, from the viewpoint of allowing satisfactory spinnability to be imparted, and allowing the formation of a coating film as a sheet, and the weight average molecular weight is more preferably 10,000 to 500,000 daltons, and still more preferably 50,000 to 350,000 daltons. The layer including the water-soluble polymer can be adjusted to have a desired collapse rate, by selecting the weight average molecular weight and the molecular weight distribution of pullulan, although this also depends on other components added. If the weight average molecular weight is excessively large, the production cost of the water-soluble polymer will increase, and the viscosity thereof tends to increase when the water-soluble compound is prepared as an aqueous solution, which reduces spinning productivity. Within the above-described range, however, these problems do not occur.

The fiber layer (B) composed of water-soluble polymer is formed of the fibers composed of the water-soluble polymer, and thus, has an increased degree of freedom of the layer, and can impart flexibility to the multilayer sheet. Furthermore, the single fiber diameter is preferably 0.001 to 100 µm. When the single fiber diameter is 0.001 µm or more, threads can be stably produced during spinning, and when the single fiber diameter is 0.1 µm or more, stability during spinning increases. When the single fiber diameter is 100 µm or less, sufficient flexibility and shape-memory properties can be imparted to the multilayer sheet. Either a long fiber or a short fiber can be used as the fiber forming the fiber layer (B) composed of water-soluble polymer.

The basis weight of the layer (A) composed of sparingly water-soluble polymer is preferably 1 to 200 g/m$^2$. The layer (A) composed of sparingly water-soluble polymer preferably satisfies the above-mentioned water resistance by itself. To improve the strength of the multilayer sheet, the basis weight is more preferably 5 g/m$^2$ or more, and particularly preferably 10 g/m$^2$ or more. Moreover, the basis weight of the layer (A) composed of sparingly water-soluble polymer is preferably 100 g/m$^2$ or less, and particularly preferably 50 g/m$^2$ or less to not impair the sufficient flexibility and shape-memory properties of the multilayer sheet.

Furthermore, the basis weight of the fiber layer (B) composed of water-soluble polymer is preferably 5 to 500 g/m$^2$. To impart sufficient flexibility and shape-memory properties to the multilayer sheet, the basis weight of the fiber layer (B) composed of water-soluble polymer is more preferably 10 g/m$^2$ or more, and particularly preferably 30 g/m$^2$ or more. Furthermore, the basis weight of the fiber layer (B) composed of water-soluble polymer is more preferably 300 g/m$^2$ or less, and particularly preferably 200 g/m$^2$ or less, because if the basis weight is increased at a certain thickness, the density will be increased to reduce flexibility, and if the basis weight is increased at a certain density, the bulkiness will increase, and in either case, the handleability of the multilayer sheet will decrease.

The basis weight of the multilayer sheet is preferably 10 to 1,000 g/m$^2$, and to satisfy all of flexibility, shape-memory properties, and handleability, the basis weight is more preferably 15 to 400 g/m$^2$, and particularly preferably 20 to 150 g/m$^2$.

The thickness of the layer (A) composed of sparingly water-soluble polymer is preferably 0.1 to 1,000 µm. The layer (A) composed of sparingly water-soluble polymer is preferably uniformly formed to impart certain water resistance, and therefore, the thickness thereof is more preferably 5 µm or more, and still more preferably 10 µm or more. Moreover, because increasing the thickness of the layer (A) composed of sparingly water-soluble polymer reduces the flexibility and shape-memory properties of the multilayer sheet, the thickness thereof is preferably 500 µm or less, and more preferably 100 µm or less.

Furthermore, the thickness of the fiber layer (B) composed of water-soluble polymer is preferably 10 to 10,000 µm. To impart sufficient flexibility and shape-memory properties to the multilayer sheet, the thickness of the fiber layer (B) composed of water-soluble polymer is more preferably 50 µm or more, and still more preferably 100 µm or more. Moreover, because increasing the thickness of the fiber layer (B) composed of water-soluble polymer increases the bulkiness of the multilayer sheet to reduce the handleability of the multilayer sheet, the thickness thereof is more preferably 5,000 µm or less, and still more preferably 1,000 µm or less.

Although the thickness of the multilayer sheet can be determined from the sum of the above-described thicknesses of the layer (A) composed of sparingly water-soluble polymer and the fiber layer (B) composed of water-soluble polymer, because these layers are integrated upon lamination, the sum of the thicknesses is smaller than that when each of the layers is prepared independently. Furthermore, when an intermediate layer other than the above layers and the other outermost layer are formed on the multilayer sheet, the thickness of the multilayer sheet is the total sum of the thicknesses of these layers and the thicknesses of the layer (A) composed of sparingly water-soluble polymer and the fiber layer (B) composed of water-soluble polymer. As described above, however, when these layers are integrated upon lamination, the sum of the thicknesses is smaller than the sum of the independent thicknesses of the respective layers. The thickness of the multilayer sheet is preferably 10 to 12,000 µm. To satisfy both flexibility and shape-memory properties, the thickness of the multilayer sheet is more preferably 50 to 2,000 µm, and still more preferably 100 to 400 µm. When the multilayer sheet is used as a backing, the above-described thicknesses of the layer (A) composed of sparingly water-soluble polymer and the fiber layer (B) composed of water-soluble polymer can be changed as appropriate, in accordance with the use of the base material integrated with the backing.

The multilayer sheet preferably has a tensile strength of 0.1 to 5.0 N/mm. With such a tensile strength, the multilayer sheet has sufficient stiffness, and when it has a thickness within the above-mentioned range of thicknesses, the multilayer sheet can be inserted through the hole of a trocar used for laparoscopic surgery. The tensile strength is more preferably 0.3 to 4.7 N/mm, and still more preferably 0.5 to 4.5 N/mm, in consideration of handleability and biodegradability.

In the multilayer sheet, the time taken from dropping of water onto the surface of the outermost layer (A) to dissolution of the other outermost layer is 10 seconds to 5 minutes. Because this time is 10 seconds or longer, the multilayer sheet can be readily handled even in the presence of moisture or blood. When the multilayer sheet is used as a backing of an anti-adhesion material, a certain time is required until it is affixed to tissues and, therefore, this time is more preferably 30 seconds or longer, and particularly preferably 1 minute or longer. On the other hand, if this time is 5 minutes or shorter, the multilayer sheet can be quickly removed after being affixed to tissues. Long-term water resistance can be achieved using, for example, a method in which the basis weight or density of a layer including a water-insoluble polymer such as the outermost layer (A) is increased. In this case, however, the texture tends to become hard and, therefore, this time is preferably 3 minutes or shorter, and particularly preferably 2 minutes or shorter.

In the multilayer sheet, at least one or more layers from each of the layer (A) composed of sparingly water-soluble polymer and the fiber layer (B) composed of water-soluble polymer are laminated, and at least one of outermost layers is the layer (A) composed of sparingly water-soluble polymer. Where the multilayer sheet has a structure of three or more layers, preferably, the layers as a whole including the layer (A) composed of sparingly water-soluble polymer as the outermost layer, the fiber layer (B) composed of water-soluble polymer as the other outermost layer or intermediate layer, and other layer(s) satisfy the above-mentioned requirement of water resistance.

As the layer(s) other than the layer (A) composed of sparingly water-soluble polymer and the fiber layer (B) composed of water-soluble polymer, a water-soluble polymer, a sparingly water-soluble polymer, or a compound not showing solubility in water can be used as appropriate, so long as the functionality, texture, and the like imparted by the layer (A) composed of sparingly water-soluble polymer and the fiber layer (B) composed of water-soluble polymer are not impaired.

The mass proportion of the layer (A) composed of sparingly water-soluble polymer in the multilayer sheet is preferably 0.1 to 50 mass %, and particularly preferably 0.1 to 20 mass %. On the other hand, the proportion of the water-soluble layer composed of the fiber layer (B) composed of water-soluble polymer is preferably 50 to 99.99 mass %, and particularly preferably 80 to 99.9 mass %.

Additionally, other intermediate layer(s) and the other outermost layer can be formed, provided that the above-described mass proportions are satisfied which do not impair the functionality of the layer (A) composed of sparingly water-soluble polymer and the fiber layer (B) composed of water-soluble polymer in the multilayer sheet.

A multilayer sheet can be obtained in which the above-described respective layers have two aspects of solubility in water, and which has flexibility, shape-memory properties and the like. The use of this multilayer sheet as a backing can improve operability of the integrated base material. Moreover, when the base material is integrated with the layer of the multilayer sheet opposite to the layer (A) composed of sparingly water-soluble polymer, the side of the layer (A) composed of sparingly water-soluble polymer of the integrated sheet shows certain water resistance, and therefore, can also be used in vivo or in an environment in which moisture is adhered.

On the other hand, after a lapse of a certain time from the adhesion of moisture to the layer (A) composed of sparingly water-soluble polymer, the water-soluble layer in contact with the base material absorbs the moisture and is dissolved, which allows the multilayer sheet to be removed from the base material. The multilayer sheet can also be removed from the base material by causing a layer having water solubility such as the fiber layer (B) composed of water-soluble polymer to absorb moisture through a cross section of the multilayer sheet. While the multilayer sheet can be suitably used as a backing of an anti-adhesion material in which operability, water resistance, and removability are required, the range of applications of the multilayer sheet is not limited thereto.

The layer (A) composed of sparingly water-soluble polymer, the fiber layer (B) composed of water-soluble polymer, and the layer(s) other than these layers can contain various additives. Specific examples of additives include a catalyst, a coloration inhibitor, a heat-resistant agent, a flame retardant, a lubricant, a stain-proofing agent, a fluorescent whitening agent, a delustering agent, a colorant, a gloss-improving agent, an antistatic agent, a fragrance, a deodorizer, an antimicrobial agent, an anti-tick agent, inorganic particles, a hemostatic agent, and a plasticizer. These additives may be added to the raw materials to form the layers, or may be applied after formation of the layers using a known method such as spraying or coating.

The multilayer sheet can be produced using a method including a first step of forming the fiber layer (B) composed of water-soluble polymer by collecting a fiber obtained by spinning a solution of a water-soluble polymer; and a second step of forming the layer (A) composed of sparingly water-soluble polymer by collecting a fiber obtained by spinning a solution of a sparingly water-soluble polymer, onto the fiber layer (B) composed of water-soluble polymer. In the method of producing the multilayer sheet, in the above-described second step, the fiber layer (B) composed of water-soluble polymer is partially dissolved when the fiber obtained by spinning the solution of the sparingly water-soluble polymer is collected.

Preferably, in the method of producing the multilayer sheet, the layer (A) composed of sparingly water-soluble polymer is formed on the fiber layer (B) composed of water-soluble polymer, using an electrospinning (which may hereinafter be referred to as ESP) method. With the electrospinning method, when an aqueous solution of the sparingly water-soluble polymer as a raw material is laminated on the fiber layer including the water-soluble polymer, the amount of evaporation of water in the atmosphere can be controlled by adjusting the discharge rate, the voltage, and the distance between the discharge and lamination. The fiber layer, therefore, can be slightly dissolved by dispersing a tiny amount of water on the fiber layer, to form a film composed of a mixture of the water-soluble polymer and the sparingly water-soluble compound. Other than electrospinning, any method in which the polymers are laminated while the amount of moisture is controlled by evaporating the solvent in the atmosphere as described above may be adopted as appropriate, such as an electrospray deposition method or a force spinning method.

As a method of producing the fiber layer (B) composed of water-soluble polymer, the electrospinning method, the electrospray deposition method, the force spinning method utilizing centrifugal force recently developed or the like which uses a solution or a melt can be used. Moreover, with a melt spinning method using a water-soluble thermoplastic polymer, filaments may be produced, and then a knit or a fabric may be formed therefrom, and methods of producing nonwoven fabrics may also be used, such as a melt blown method, a spun-bonding method, and a needle-punching method.

The method of producing the layer (A) composed of sparingly water-soluble polymer or the fiber layer (B) composed of water-soluble polymer may be any method capable of forming a layer from a solution or a melt. The layer may also be formed using a composite fiber composed of two or more water-soluble thermoplastic resins.

Furthermore, where a layer other than the layer (A) composed of sparingly water-soluble polymer and the fiber layer (B) composed of water-soluble polymer is provided in the multilayer sheet, the layer can be produced using a method similar to that for the layer (A) composed of sparingly water-soluble polymer or the fiber layer (B) composed of water-soluble polymer described above, and a knit or a fabric may also be used.

When the layer (A) composed of sparingly water-soluble polymer and the other intermediate layer(s) are formed on the fiber layer (B) composed of water-soluble polymer or the water-soluble polymer intermediate layer, the fiber layer (B) composed of water-soluble polymer serves to cause the layers to be adhered. Thus, the handleability of the multilayer sheet can be improved, and transportability that is insufficient only with the layer (A) composed of sparingly water-soluble polymer can be compensated for. Furthermore, when the layer (A) composed of sparingly water-soluble polymer is formed on a transport sheet, there is no risk of possible adhesion between the transport sheet and the layer (A) composed of sparingly water-soluble polymer. Thus, the multilayer sheet can be readily peeled from the transport sheet, and can be easily applied to the production line, which is preferable.

As a method of forming the layer (A) composed of sparingly water-soluble polymer or the other intermediate layer(s), the ESP method, the electrospray deposition method or the like is preferably used. With these methods, a solution or a melt is dispersed and drawn, and simultaneously, moisture is evaporated in the air, or the melt is solidified. By controlling the amount of moisture and the amount of melting, the layer (A) composed of sparingly water-soluble polymer and the other intermediate layer(s) can be laminated together with the liquid on the water-soluble polymer layer, without excessively dissolving the layer. In this way, upon vaporization or solidification of the liquid content, a minute film can be formed on the water-soluble polymer layer to improve the water resistance of the multilayer sheet.

On the other hand, where a film of the layer (A) composed of sparingly water-soluble polymer is formed without dissolving the water-soluble polymer layer, although precise adjustment of the solution or melt and production environment are required, a method of forming the film such as a spin coating method, a spraying method, a roll coating method, a die coating method, or a wire bar method is also preferably used, from the viewpoint of volume production. Separately prepared layers may be laminated. In this case, the adhesiveness between the layers is somewhat poor and, therefore, during lamination, a small amount of water or an aqueous solution containing an adhesive may be added to such a degree that does not cause excessive dissolution.

Alternatively, the fiber layer (B) composed of water-soluble polymer and the other intermediate layer(s) may be formed on the layer (A) composed of sparingly water-soluble polymer. In this case, because the layer (A) composed of sparingly water-soluble polymer is unlikely to dissolve in water, when the fiber layer (B) composed of water-soluble polymer is laminated thereon, the layer (A) composed of sparingly water-soluble polymer is not dissolved. Thus, the fiber layer (B) composed of water-soluble polymer as an intermediate layer or outermost layer and the other layer(s) may be formed, and then the layer (A) composed of sparingly water-soluble polymer may be formed thereon.

A specific example of preparation of the layer (A) composed of sparingly water-soluble polymer and the fiber layer (B) composed of water-soluble polymer using the ESP method will now be described. An aqueous solution of the water-soluble polymer is dispersed onto a collection electrode coated with an insulator, grounded, or provided with opposite charge to that of the aqueous solution, for example, to form the fiber layer (B) composed of water-soluble polymer. Then, an aqueous solution of the sparingly water-soluble polymer is dispersed to form the layer (A) composed of sparingly water-soluble polymer. The multilayer sheet is thus obtained.

ESP conditions are preferably such that the voltage is 15 to 100 kV, the angle between the syringe and the collection electrode during spinning is −30 to 60 degrees, the discharge rate is 3 to 100 ml/hr, and the inner diameter of the syringe is 10 to 10,000 µm. Moreover, to reduce variations in the width direction of the layer, the base on which the syringe is mounted may be moved back and forth in parallel with the width direction of the collection electrode, and to readily disperse the aqueous solution onto the collection electrode, an electrode provided with opposite charge to that of the aqueous solution may be mounted around the syringe and the collection electrode.

The distance between a nozzle tip and the collection electrode during spinning using the ESP method is preferably 3 to 10 cm, particularly preferably 5 to 9 cm, and even more preferably 6 to 8 cm. When the distance between the nozzle tip and the collection electrode is 3 cm or more, the possibility of the occurrence of a spark between the nozzle tip and the collection electrode can be reduced to prevent a failure of the ESP apparatus. Moreover, when the distance between the nozzle tip and the collection electrode is 10 cm or less, the fiber obtained by spinning a solution of the sparingly water-soluble polymer can be collected onto the fiber layer (B) composed of water-soluble polymer on the collection electrode, before the moisture contained in the solution or melt is evaporated in the air, or the melt is solidified. When the layer (A) composed of sparingly water-soluble polymer is formed, the fiber layer (B) composed of water-soluble polymer is partially dissolved in the solvent, to readily form a thin-film structure partially having a defect or having an uneven thickness, which has a nano-order or submicron-order thickness. The thin film facilitates achievement of desired water resistance. Examples of advantages of reducing the thickness of the layer (A) composed of sparingly water-soluble polymer include a reduction in the amount of raw materials used, a reduction in the spinning time, and sufficient flexibility imparted to the multilayer sheet.

The spinning conditions may be changed during formation of the layer. For example, reducing the voltage makes the single fiber diameter greater to increase the bulkiness of the layer, while increasing the voltage makes the fiber diameter smaller to reduce the bulkiness of the layer. Thus, the time from adhesion of moisture to the surface of the layer (A) composed of sparingly water-soluble polymer to entry of the moisture into the lower layer can be controlled to some extent. Moreover, when the inner diameter of the nozzle is smaller, a droplet at the tip is smaller, and hence, the single fiber diameter tends to be smaller. The above-described spinning conditions can be changed as appropriate so long as the above-mentioned requirement of water resistance is satisfied.

The water resistance satisfying the above-mentioned requirement can be imparted mainly by controlling the raw materials and spinning conditions. Specifically, by controlling the molecular weight, the degree of polymerization, the substituents, the degree of substitution, and the solution concentration of the sparingly water-soluble polymer as a raw material, the solubility in water at ordinary temperature, the spinnability during spinning, and the like of the polymer itself can be controlled. Moreover, in the ESP method, for example, the spinning conditions include the applied voltage, the discharge rate, the distance and the angle between the syringe and the collection electrode, as well as the temperature and humidity. Furthermore, equalization in the length direction and the width direction is also required.

In particular, it is preferred that the layer (A) composed of sparingly water-soluble polymer is formed by dispersing, onto the fiber layer (B) composed of water-soluble polymer, the sparingly water-soluble polymer that has not completely evaporated, using the ESP method. In a common ESP method, the compound that has completely or almost completely evaporated is dispersed onto the fiber layer (B) composed of water-soluble polymer. When, however, the sparingly water-soluble polymer is used as the solute, spinnability tends to slightly deteriorate. On the other hand, when the sparingly water-soluble polymer solution from which the solvent has not completely evaporated is laminated on the fiber layer (B) composed of water-soluble polymer, it can form a layer partially containing fibers or containing many film-like layers not containing fibers. Thus, sufficient water resistance can be imparted to the multilayer sheet having the layer (A) composed of sparingly water-soluble polymer as an outermost layer. This layer can be formed by adjusting the above-mentioned spinning conditions.

The layer (A) composed of sparingly water-soluble polymer formed using a method such as the above-described ESP method may partially contain fibers. However, as the amount of fibers in the layer (A) composed of sparingly water-soluble polymer increases, the water permeability thereof is improved, which reduces the water resistance of the multilayer sheet. The amount of fibers can be increased within a range where the water resistance is satisfied.

One example of forming fibers in the layer (A) composed of sparingly water-soluble polymer is a method in which the sparingly water-soluble polymer from which the solvent has completely evaporated is spun using the ESP method. However, many voids will be present in the layer (A) composed of sparingly water-soluble polymer thus formed. Although the fibers themselves of the sparingly water-soluble polymer are unlikely to dissolve, water is very likely to pass through the fibers. To allow the layer (A) composed of sparingly water-soluble polymer to express water resistance when it has a fibrous structure, water resistance may be imparted by compressing the layer (A) composed of sparingly water-soluble polymer, using calendering or the like, to increase the density thereof. If, however, the density is excessively increased, the texture of the layer (A) composed of sparingly water-soluble polymer or the multilayer sheet tends to become hard. Alternatively, water resistance may be imparted by using a sparingly water-soluble thermoplastic polymer for the layer (A) composed of sparingly water-soluble polymer, and forming the compound into a film through thermal fusion on the surface. Similarly, in this case, however, hardening of the texture or pyrolysis of other layers, for example, tends to occur. Although these problems are present, processing to impart water resistance can be applied so long as it does not interfere with imparting sufficient flexibility or shape-memory properties to the multilayer sheet.

Preferably, the method of producing the multilayer sheet includes only the ESP method to form each of the layers, because it may use only water as the solvent, and is therefore environmentally friendly.

FIG. 1 is a perspective view illustrating the structure of a multilayer sheet. In FIG. 1, the multilayer sheet is composed of a layer (A) composed of sparingly water-soluble polymer and a fiber layer (B) composed of sparingly water-soluble polymer.

Figure 2:
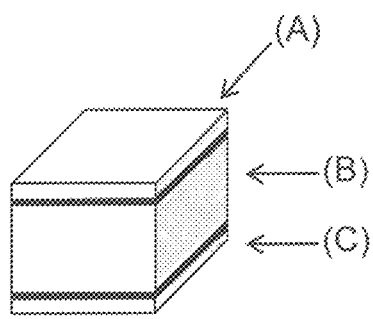
FIG. 2 shows a perspective view showing one exemplary structure of an integrated sheet.

FIG. 2 is a perspective view illustrating the structure of an integrated sheet. In FIG. 2, the outermost layers of the integrated sheet are each composed of the layer (A) composed of sparingly water-soluble polymer or a base material (C) composed of sparingly water-soluble polymer, and the fiber layer (B) composed of water-soluble polymer is present between the two layers.

The integrated sheet is a sheet in which the multilayer sheet and the base material (C) composed of sparingly water-soluble polymer are integrally laminated, and the outermost layers are preferably formed by the layer (A) composed of sparingly water-soluble polymer and the base material (C) composed of sparingly water-soluble polymer. With this structure, because both the outermost layers are the layers each including the sparingly water-soluble polymer, they do not become sticky when moisture or blood is adhered thereto, thus leading to sufficient handleability. Furthermore, when the integrated base material (C) composed of sparingly water-soluble polymer is affixed to a target place such as wound tissues, and then water is added from a side thereof, the fiber layer including the water-soluble polymer is readily dissolved so that the backing of the multilayer sheet can be quickly removed.

Examples of compounds forming the base material (C) composed of sparingly water-soluble polymer include polypeptides, polyamino acids, polysaccharides, aliphatic polyesters, poly(ester-ethers), poly(ester-carbonates, polyorthoesters), polycarbonates, poly(amide esters), poly($\alpha$-cyanoacrylates), and polyphosphazenes. These polymers can be used singly, or as a mixture of two or more.

Specifically, polypeptides such as albumin, fibrinogen, collagen, gelatin, and derivatives thereof; polyamino acids such as poly-L-glutamic acid, poly-L-leucine, poly-L-lysine, and derivatives thereof; aliphatic polyesters such as poly($\beta$-hydroxyalkanoates), polyglycolide, polylactide, polylactic acid, polyglactin, poly($\alpha$-malic acid), poly-$\epsilon$-caprolactone, and derivatives thereof; poly(ester-ethers) such as poly(1,4-dioxane-2-one), poly(1,4-dioxepan-7-one), and derivatives thereof; poly(ester-carbonates) such as poly(lactide-co-glycolide), poly(glycolide-co-1,3-dioxane-2-one), and derivatives thereof; polyanhydrides such as poly(sebacic anhydride), poly[$\omega$-(carboxyphenoxy)alkyl carboxylic acid anhydride], and derivatives thereof; polycarbonates such as poly(1,3-dioxane-2-one) and derivatives thereof; poly(amide esters) such as polydepsipeptides and derivatives thereof; poly($\alpha$-cyanoacrylates) such as poly (ethyl $\alpha$-cyanoacrylate) and derivatives thereof; and polyphosphazenes such as polyphosphazenes and derivatives thereof; and the like can be used. Among the above, aliphatic polyesters are preferably used, and polylactic acid having satisfactory biocompatibility is more preferable. Moreover, the same polymer as that of the layer (A) composed of sparingly water-soluble polymer can also be used.

The base material (C) composed of sparingly water-soluble polymer is preferably a functional base material. Examples of functional base materials include biocompatible base materials having an anti-adhesion function that can serve as a physical barrier between tissues during surgery; those used in medicines, medical supplies, or the like having a hemostatic component, a medicinal component, or an antimicrobial component; those used in cosmetics or the like having a medicinal component or an antimicrobial component; and those used in electronic information materials having an antistatic component or a conductive component. The base material (C) composed of sparingly water-soluble polymer can also be applied to base materials having functionalities other than the above, and in particular, is preferably a base material having an anti-adhesion function. Depending on the purpose, a layer other than the layer (A) composed of sparingly water-soluble polymer and a base material may be used as outermost layers; a plurality of multilayer sheets may be used as both outermost layers, and a base material may be used as an inner layer; or a plurality of base materials may be used as both outermost layers, and a multilayer sheet may be used as an inner layer. Any combination of multilayer sheets and base materials may be used.

The anti-adhesion material includes no toxic materials, and is harmless to a human body. The anti-adhesion material serves as a physical barrier that prevents adhesion formation while being concentrated on tissues or an organ site within the body during wound healing. After the healing is completed, it is degraded within the human body, absorbed, metabolized, and excreted. In this case, the above-described degradation period is particularly preferably 7 days or longer, although it can be changed by adjusting the proportion of the surface area/volume of the base material layer, the composition of the polymer used, formation of the crystal structure, the thickness of the polymer layer, the degree of crosslinking, and the like.

After formation of the layer (A) composed of sparingly water-soluble polymer or the fiber layer (B) composed of water-soluble polymer, or after the integration of the base material (C) composed of sparingly water-soluble polymer, a compression or adhesion treatment can be applied thereto, as required. With a calendering treatment, for example, fluff on the surface of the fiber layer (B) composed of water-soluble polymer can be reduced, or the texture can be changed into a paper-like or film-like texture, and increasing the density can improve the water resistance, tolerance to friction or piercing, tensile strength, and the like. Moreover, with an embossing treatment, effects equivalent to those with the calendering treatment, as well as an increased strength against bending or distortion can be expected. Moreover, the front or rear side of the multilayer sheet or the integrated sheet can be readily distinguished by forming a pattern such as projections and depressions or printing on the surface. A pattern can also be formed using a method such as casting, and the front and rear sides may each have a different pattern.

The basis weight of the integrated sheet is determined from the sum of the basis weight of the above-described multilayer sheet composed of the layer (A) composed of sparingly water-soluble polymer, the fiber layer (B) composed of water-soluble polymer, and the intermediate layer(s) other than these layers, and the basis weight of the base material (C) composed of sparingly water-soluble polymer. However, the basis weight of the base material (C) composed of sparingly water-soluble polymer is sufficiently smaller than that of the multilayer sheet and, therefore, the basis weight of the integrated sheet is preferably 10 to 1,000 g/m$^2$, as with the multilayer sheet, and more preferably 15 to 400 g/m$^2$, and particularly preferably 20 to 150 g/m$^2$ to satisfy all of flexibility, shape-memory properties and handleability.

The thickness of the integrated sheet is determined from the sum of the thickness of the above-described multilayer sheet composed of the layer (A) composed of sparingly water-soluble polymer, the fiber layer (B) composed of water-soluble polymer, and the intermediate layer(s) other than these layers, and the thickness of the base material (C) composed of sparingly water-soluble polymer. However, because these layers are integrated upon lamination, the sum of the thicknesses is smaller than that when each of the layers is prepared independently. Moreover, the thickness of the base material (C) composed of sparingly water-soluble polymer is sufficiently smaller than that of the multilayer sheet and, therefore, the thickness of the integrated sheet is preferably 10 to 12,000 μm, as with the multilayer sheet. To satisfy both flexibility and shape-memory properties, the thickness of the integrated sheet is more preferably 50 to 2,000 μm, and still more preferably 100 to 400 μm.

Next, one exemplary method of producing the integrated sheet will be described.

While the method of producing the base material (C) composed of sparingly water-soluble polymer is not particularly limited, examples thereof include the following:

(1) A laminated film having the base material (C) composed of sparingly water-soluble polymer and a layer including a water-soluble resin, or a single film of the base material (C) composed of sparingly water-soluble polymer, is formed on a plastic film. While the method of laminating the base material (C) composed of sparingly water-soluble polymer and the layer including the water-soluble resin is not particularly limited, examples thereof include spin coating, spraying, roll coating, die coating, wire bar, gravure coating, ink-jet, and silk screen printing.

(2) The formed laminated film or single film is peeled from the plastic film.

(3) The obtained laminated film or single film is laminated and fixed to a multilayer sheet, thus giving an integrated sheet.

While the method of laminating the film and the multilayer sheet is not particularly limited, examples thereof include: a method in which water or the like is sprayed onto the surface of the layer including the water-soluble resin in the laminated film of the layer including the water-soluble resin and the base material (C) composed of sparingly water-soluble polymer, or onto the surface of the fiber layer (B) composed of water-soluble polymer in the multilayer sheet, to dissolve the surface, and the dissolved surface and the surface of the respective layer including the water-soluble resin are contacted and welded together; and a method in which water is sprayed onto the surface of the single film of the base material (C) composed of sparingly water-soluble polymer, and then this surface is contacted with the surface of the fiber layer (B) composed of water-soluble polymer in the multilayer sheet, to dissolve the surface of the fiber layer (B) composed of water-soluble polymer in contact with the base material (C) composed of sparingly water-soluble polymer, to achieve adhesion therebetween.

The method of integrating the multilayer sheet composed of the layer (A) composed of sparingly water-soluble polymer and the fiber layer (B) composed of water-soluble polymer, with the base material (C) composed of sparingly water-soluble polymer, may be as follows. The base material (C) composed of sparingly water-soluble polymer may be formed on the other outermost layer of the multilayer sheet, rather than the layer (A) composed of sparingly water-soluble polymer, thus forming an integrated sheet. Alternatively, after the base material (C) composed of sparingly water-soluble polymer is formed, it may be laminated to the multilayer sheet with an adhesive or the like, thus forming an integrated sheet.

As described above, the multilayer sheet can be used in vivo or in an environment in which moisture is adhered, and can be preferably used as a protective material, coating material, or sealant for an organ surface or a wound site. The integrated sheet can be preferably used for medical supplies such as an anti-adhesion material, artificial dura mater, a hemostatic material, and a scaffold material. Furthermore, when a water-soluble or sparingly water-soluble base material is laminated on the multilayer sheet or integrated sheet, properties such as strength and water resistance can be imparted to the base material for improvement, and thus, the multilayer sheet or integrated sheet can also be preferably used in cosmetics and electronic materials.

EXAMPLES

Next, the multilayer sheet and the integrated sheet will be described in more detail, with reference to examples.

1. Evaluation Method

Multilayer sheets according to Examples 1 to 6 and Comparative Examples 1 to 4 were evaluated as described in (1) to (6) below, and integrated sheets were evaluated as described in (7) below.

(1) Evaluation of Basis Weight

Masses of each of the fiber layer (B) composed of water-soluble polymer and the multilayer sheet, each measuring 15 cm in length by 15 cm in width, were measured at three points, and each of the obtained values was converted into a value per $m^2$, and an average value thereof was determined as the basis weight ($g/m^2$). The basis weight of the layer (A) composed of sparingly water-soluble polymer was calculated by subtracting the basis weight ($g/m^2$) of the fiber layer (B) composed of water-soluble polymer, from the basis weight ($g/m^2$) of the multilayer sheet.

(2) Evaluation of Average Fiber Diameter

The surface of each of the layer (A) composed of sparingly water-soluble polymer and the fiber layer (B) composed of water-soluble polymer as an observation surface was observed with a scanning electron microscope (SEM, model VE-7800 manufactured by Keyence Corporation) at 1,000 or 5,000 magnifications, 100 fibers were randomly selected from the observed fibers, and an average value of measured values of the fiber diameter was determined as the fiber diameter (μm). Cases where almost no fibers were present were determined as being unmeasurable.

(3) Evaluation of Thickness

A cross section of the multilayer sheet as an observation surface was observed with a scanning electron microscope (SEM, model VE-7800 manufactured by Keyence Corporation) at 100 or 1,000 magnifications, ten points were randomly selected from thicknesses of each of the observed layers, and an average value of the measured values was determined as the thickness (μm).

(4) Evaluation of Water Resistance

Water resistance was evaluated based on a method similar to that according to JIS L 1907 (2010). As in the dropping method, the height from the surface of a specimen to the tip of a burette was adjusted to 10 mm, and one droplet of water was dropped from the burette. The start time was defined as the time when the droplet of water reached the surface of the outermost layer (A) of the specimen, and the end time was defined as the time when the water after penetrating through the outermost layer (A), a lower layer thereof, and then the other outermost layer, which was the lowermost layer, dissolved the other outermost layer. Then, the time taken from the start time to the end time was measured. The term "dissolved" means the state where 20% of the polymer forming the layer was dissolved into water, or the state where the polymer collapsed without being able to maintain its layer shape. Whether the polymer was dissolved or not was determined through visual observation from various directions such as the outermost layer (A) side and a cross section side.

(5) Evaluation of Appearance

The appearance quality of the multilayer sheet was evaluated through sensory evaluations by five specialists, and the surface quality and the texture were evaluated using the following three-point rating method, with good and fair being acceptable.

Surface quality: Good, Fair, and Poor.

Texture: Good (soft); Fair (slightly hard); and Poor (hard).

(6) Tensile Strength

In accordance with 6.3.1 "at standard times" of 6.3 "Tensile strength and elongation" in JIS L 1913 (2010) "Test methods for nonwovens" (note, however, that the specimen size, the length of the specimen between grips, and the tensile rate were changed), tensile strength was measured using the following method.

In the longitudinal direction of the multilayer sheet (length direction of the multilayer sheet), specimens measuring 200 mm in length by 30 mm in width were sampled at three points. The specimens were subjected to a tensile test in a constant-rate-of-extension type tensile testing machine, under a length of the specimen between grips of 100 mm and a tensile rate of 200±10 mm/min, strengths (N) at the maximum load until breakage were measured, and a value obtained by dividing an average value thereof by the width of 30 mm was determined as the tensile strength (N/mm).

(7) Evaluation of Removability

The integrated sheet was affixed to a target such that the base material (C) composed of sparingly water-soluble polymer faced the target, and 10 ml of water was added to the integrated sheet from a cross section side thereof. Then, whether or not the base material (C) composed of sparingly water-soluble polymer and the multilayer sheet were removed was evaluated, with good being acceptable.

Removability: Good (quickly removed); Fair (removed with time); Poor (not removed).

2. Preparation and Evaluation of a Sheet

Example 1

(1) Spinning of a Fiber Layer (B) Composed of Water-Soluble Polymer

To 80 mass parts of water, 20 mass parts of pullulan having a weight average molecular weight of 200,000 (Hayashibara Co., Ltd.) was added while stirring at a room temperature of 20° C., thus giving an aqueous solution of pullulan having a concentration of 20%.

Figure 3:
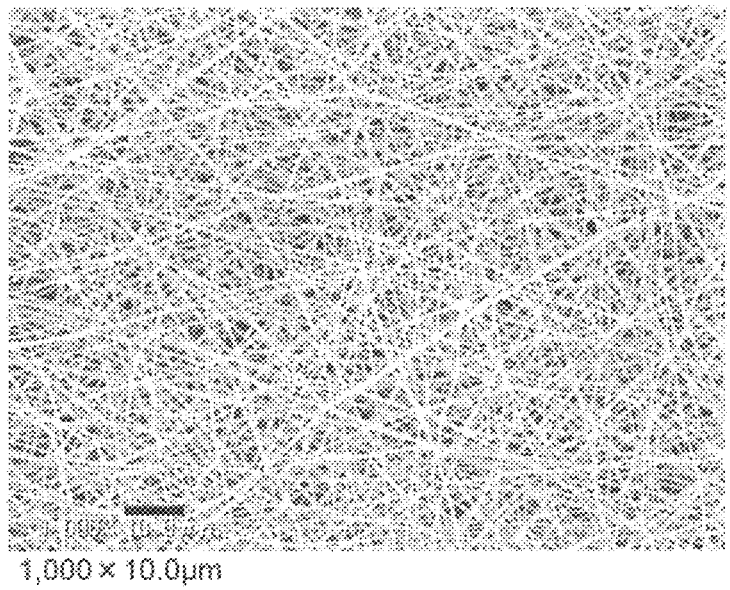
FIG. 3 shows a photograph (1,000 magnifications) of the surface of a fiber layer (B) composed of water-soluble polymer obtained in Example 1.

Using an ESP apparatus "NEU" manufactured by Kato Tech Co., Ltd., the aqueous solution of pullulan was spun using an ESP method, at an atmosphere temperature of 20° C. and an atmosphere humidity of 40% RH. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 1 m/min, the discharge rate was 0.04 cm/min, the applied voltage was 23.5 kV, the traverse rate was 3.3 cm/min, the traverse width was 21 cm, and the distance between the nozzle tip and the collection electrode was 15 cm. Pullulan fibers spun using the ESP method were collected in the form of a nonwoven fabric, and an SEM observation thereof confirmed the formation of ultrafine fibers. FIG. 3 shows a photograph (1,000 magnifications) of the surface of the fiber layer (B) composed of water-soluble polymer.

(2) Spinning of a Layer (A) Composed of Sparingly Water-Soluble Polymer

To 94 mass parts of water, 6 mass parts of PVA having a degree of saponification of 99.0% or more (Japan Vam & Poval Co., Ltd.; product number: JC-40) was added while stirring at a room temperature of 25° C., and dissolved with stirring at a temperature of 95° C. The solution was slowly cooled to a temperature of 20° C., thus giving an aqueous solution of PVA having a concentration of 6%. The aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 $cm^3$/min, the applied voltage was 36.0 kV, the traverse rate was 20 cm/min, the traverse width was 15 cm, and the distance between the nozzle tip and the collection electrode was 7 cm.

Figure 4:
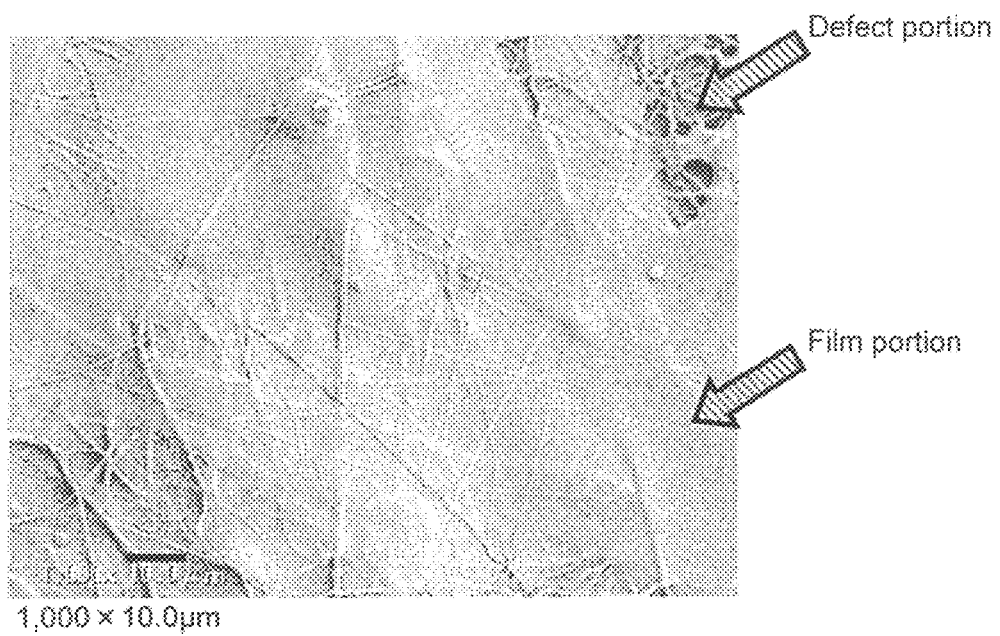
FIG. 4 shows a photograph (1,000 magnifications) of the surface of a layer (A) composed of sparingly water-soluble polymer obtained in Example 1.
Figure 5:
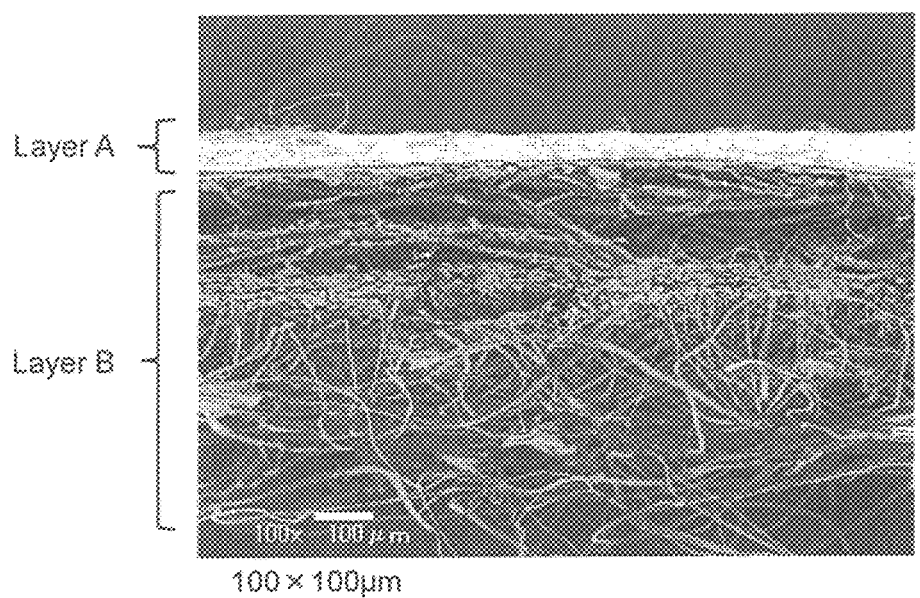
FIG. 5 shows a photograph (100 magnifications) of a cross section of a multilayer sheet obtained in Example 1.

The PVA fibers spun using the ESP method were collected in the form of a nonwoven fabric, and an SEM observation thereof confirmed formation of a film and a small amount of ultrafine fibers. FIG. 4 shows a photograph (1,000 magnifications) of the surface of the layer (A) composed of sparingly water-soluble polymer. FIG. 5 shows a photograph (100 magnifications) of a cross section of the multilayer sheet.

(3) Preparation of an Integrated Sheet on which a Base Material (C) Composed of Sparingly Water-Soluble Polymer was Laminated Using a warming-type homogenizer, a water-soluble resin, i.e., pullulan (sold by Hayashibara Co., Ltd.; product number: P1-20), was dissolved in water to prepare a water-soluble resin emulsion, and applied to one surface of a PET film using an applicator method such that the thickness after drying became 3 μm. The solution was dried at 90° C. for 20 seconds within a hot air dryer, thus preparing a layer including the water-soluble resin on the PET film.

A solution in which poly-DL-lactic acid (PURAC; product number: PURASORB PDL20) was dissolved in ethyl acetate was applied to the above-described layer including the water-soluble resin using a metaling bar such that the thickness after drying became 150 nm, and dried at 80° C. for 20 seconds within a hot air dryer, thus preparing a laminated film in which the layer including the water-soluble resin and the base material (C) composed of sparingly water-soluble polymer were laminated on the PET film.

The above-described laminated film was peeled from the PET film, and pure water was sprayed with an atomizer in an amount of 5 g/$m^2$ onto the layer including the water-soluble resin. Then, the film was quickly laminated to the fiber layer (B) composed of water-soluble polymer of the multilayer sheet produced in (2) above, thus preparing an integrated sheet.

(4) Evaluation Results

The evaluation results for the multilayer sheet were as shown in Tables 1 and 2, and the evaluation results for the integrated sheet were as shown in Table 2. The multilayer sheet was satisfactory in water resistance, surface quality, and texture, and the integrated sheet was also satisfactory in removability.

Example 2

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 96 mass parts of water, 15 mass parts of PVA having a degree of saponification of 99.0% or more (Japan Vam & Poval Co., Ltd.; product number: JC-40) was added while stirring at a room temperature of 20° C., and dissolved with stirring at a temperature of 95° C. The solution was slowly cooled to 20° C., thus giving an aqueous solution of PVA having a concentration of 6%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 $cm^3$/min, the applied voltage was 3.0 kV, the traverse rate was 20 cm/min, the traverse width was 5 cm, and the distance between the nozzle tip and the collection electrode was 10 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. The multilayer sheet was satisfactory in water resistance and surface quality, although it had a rather hard texture. The integrated sheet was satisfactory in removability.

Example 3

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 90 mass parts of water, 10 mass parts of PVA having a degree of saponification of 98.0 to 99.0% (Japan Vam & Poval Co., Ltd.; product number: JF-20) was added while stirring at a room temperature of 20° C., and dissolved with stirring at a temperature of 95° C. The solution was slowly cooled to 20° C., thus giving an aqueous solution of PVA having a concentration of 10%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 $cm^3$/min, the applied voltage was 32.0 kV, the traverse rate was 20 cm/min, the traverse width was 15 cm, and the distance between the nozzle tip and the collection electrode was 7 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. The multilayer sheet was satisfactory in water resistance, surface quality, and texture, and the integrated sheet was also satisfactory in removability.

Example 4

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 80 mass parts of water, 15 mass parts of PVA having a degree of saponification of 95.5 to 97.5% (Japan Vam & Poval Co., Ltd.; product number: JM-17) was added while stirring at a room temperature of 20° C., and dissolved with stirring at a temperature of 95° C. The solution was slowly cooled to 20° C., thus giving an aqueous solution of PVA having a concentration of 15%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 $cm^3$/min, the applied voltage was 28.0 kV, the traverse rate was 20 cm/min, the traverse width was 15 cm, and the distance between the nozzle tip and the collection electrode was 7 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. Although the multilayer sheet had rather low water resistance and a rather hard texture, it was satisfactory in other evaluations such as surface quality.

Example 5

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 80 mass parts of water, 20 mass parts of PVA having a degree of saponification of 92.5 to 94.5% (Japan Vam & Poval Co., Ltd.; product number: JT-13Y) was added while stirring at a room temperature of 20° C., and dissolved with stirring at a temperature of 95° C. The solution was slowly cooled to 20° C., thus giving an aqueous solution of PVA having a concentration of 20%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 $cm^3$/min, the applied voltage was 28.0 kV, the traverse rate was 20 cm/min, the traverse width was 15 cm, and the distance between the nozzle tip and the collection electrode was 7 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. Although the multilayer sheet had rather low water resistance and a rather hard texture, it was satisfactory in other evaluations such as surface quality.

Example 6

(1) Spinning of a Fiber Layer (B) Composed of Water-Soluble Polymer

To 80 mass parts of water, 20 mass parts of PVA having a degree of saponification of 86.5 to 89.0% (The Nippon Synthetic Chemical Industry Co., Ltd.; product number: GL-05) was added while stirring at a room temperature of 20° C., and dissolved with stirring at a temperature of 90° C. The solution was slowly cooled to 20° C., thus giving an aqueous solution of PVA having a concentration of 20%.

Using the ESP apparatus "NEU" manufactured by Kato Tech Co., Ltd., the aqueous solution of PVA was spun using the ESP method, at an atmosphere temperature of 20° C. and an atmosphere humidity of 40% RH. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 1 m/min, the discharge rate was 0.04 $cm^3$/min, the applied voltage was 23.5 kV, the traverse rate was 3.3 cm/min, the traverse width was 21 cm, and the distance between the nozzle tip and the collection electrode was 15 cm.

Fibers spun using the ESP method were collected in the form of a nonwoven fabric, and an SEM observation thereof confirmed formation of ultrafine fibers.

(2) Spinning of a Layer (A) Composed of Sparingly Water-Soluble Polymer

The aqueous solution of PVA described in Example 1 was spun using the ESP method under the same conditions onto the PVA nonwoven fabric sheet, thus preparing a multilayer sheet. PVA was collected in the form of a nonwoven fabric using ESP, and an SEM observation thereof confirmed formation of a film and a small amount of ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. The multilayer sheet was satisfactory in water resistance, surface quality, and texture, and the integrated sheet was also satisfactory in removability.

Example 7

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 85 mass parts of water, 15 mass parts of PVA having a degree of saponification of 98.0 to 99.0% (Japan Vam & Poval Co., Ltd.; product number: JF-10) was added while stirring at a room temperature of 20° C., and dissolved with stirring at a temperature of 95° C. The solution was slowly cooled to 20° C., thus giving an aqueous solution of PVA having a concentration of 15%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.01 cm$^3$/min, the applied voltage was 28.0 kV, the traverse rate was 20 cm/min, the traverse width was 15 cm, and the distance between the nozzle tip and the collection electrode was 7 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. Although the multilayer sheet was satisfactory in water resistance, it had a hard texture. The integrated sheet was satisfactory in removability.

Example 8

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 73 mass parts of water, 27 mass parts of PVA having a degree of saponification of 99.1% (Japan Vam & Poval Co., Ltd.; product number: JF-05DH) was added while stirring at a room temperature of 20° C., and dissolved with stirring at a temperature of 95° C. The solution was slowly cooled to 20° C., thus giving an aqueous solution of PVA having a concentration of 27%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.01 cm$^3$/min, the applied voltage was 23.0 kV, the traverse rate was 20 cm/min, the traverse width was 15 cm, and the distance between the nozzle tip and the collection electrode was 5.5 cm. The PVA fibers spun using the ESP method were collected in the form of a nonwoven fabric, and an SEM observation thereof confirmed formation of a film and ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. While the multilayer sheet had rather low water resistance and a hard texture, the integrated sheet was satisfactory in removability.

Example 9

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 78 mass parts of water, 22 mass parts of PVA having a degree of saponification of 99.1% (Japan Vam & Poval Co., Ltd.; product number: JF-05DH) was added while stirring at a room temperature of 20° C., and dissolved with stirring at a temperature of 95° C. The solution was slowly cooled to 20° C., thus giving an aqueous solution of PVA having a concentration of 22%.

As in Example 1, the aqueous solution of PVA was spun onto the pullulan nonwoven fabric sheet, using the ESP method, thus preparing a multilayer sheet. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.01 cm$^3$/min, the applied voltage was 36.0 kV, the traverse rate was 20 cm/min, the traverse width was 15 cm, and the distance between the nozzle tip and the collection electrode was 15 cm. The PVA fibers spun using the ESP method were collected in the form of a nonwoven fabric, and an SEM observation thereof confirmed formation of ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. Although the multilayer sheet had rather low water resistance, it was satisfactory in texture and surface quality, and the integrated sheet was also satisfactory in removability.

Comparative Example 1

(1) Spinning of a Fiber Layer (B) Composed of Water-Soluble Polymer

A pullulan nonwoven fabric was produced as in Example 1.

(2) Preparation of an Integrated Sheet on which a Base Material (C) Composed of Sparingly Water-Soluble Polymer was Laminated An integrated sheet was prepared as in Example 1, except that the layer including the water-soluble resin of the laminated film was laminated to the above-described fiber layer (B) composed of water-soluble polymer.

(3) Evaluation Results

The evaluation results for the pullulan nonwoven fabric prepared in (1) above alone were as shown in Tables 1 and 2, and the evaluation results for the integrated sheet obtained using the pullulan nonwoven fabric were as shown in Table 2. The pullulan nonwoven fabric had no water resistance, and with regard to the surface quality of the integrated sheet, wrinkles occurred due to shrinkage of the pullulan nonwoven fabric.

Comparative Example 2

(1) Spinning of a Layer (A) Composed of Sparingly Water-Soluble Polymer

Using the ESP apparatus "NEU" manufactured by Kato Tech Co., Ltd., the aqueous solution of PVA described in Example 1 was spun using the ESP method, at an atmosphere temperature of 20° C. and an atmosphere humidity of 40% RH. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.10 cm$^3$/min, the applied voltage was 36.0 kV, the traverse rate was 20 cm/min, the traverse width was 15 cm, and the distance between the nozzle tip and the collection electrode was 7 cm. The PVA fibers spun using the ESP method were collected in the form of a nonwoven fabric, and an SEM observation thereof confirmed formation of a film and a small amount of ultrafine fibers.

(2) Preparation of an Integrated Sheet on which a Base Material (C) Composed of Sparingly Water-Soluble Polymer was Laminated An integrated sheet was prepared as in Example 1, except that the layer including the water-soluble resin of the laminated film was laminated to the above-described layer (A) composed of sparingly water-soluble polymer.

(3) Evaluation Results

The evaluation results for the PVA fibers in the form of a nonwoven fabric prepared in (1) above alone were as shown in Tables 1 and 2, and the evaluation results for the integrated sheet obtained using the PVA fibers in the form of a nonwoven fabric were as shown in Table 2. Although the PVA fibers in the form of a nonwoven fabric was satisfactory in water resistance, it had a hard texture, and the integrated sheet also had poor removability.

Comparative Example 3

(1) Spinning of a Fiber Layer (B) Composed of Water-Soluble Polymer

To 80 mass parts of water, 20 mass parts of PVA having a degree of saponification of 86.5 to 89.0% (The Nippon Synthetic Chemical Industry Co., Ltd.; product number: GL-05) was added while stirring at a room temperature of 20° C., and dissolved with stirring at a temperature of 90° C. The solution was slowly cooled to 20° C., thus giving an aqueous solution of PVA having a concentration of 20%.

The above-described aqueous solution of PVA, instead of the aqueous solution of pullulan, was spun using the ESP method, under the same conditions as those described in Example 1 (1). The PVA fibers spun using the ESP method were collected in the form of a nonwoven fabric, and an SEM observation thereof confirmed formation of a film and ultrafine fibers.

(2) Preparation of an Integrated Sheet on which a Base Material (C) Composed of Sparingly Water-Soluble Polymer was Laminated An integrated sheet was prepared as in Example 1, except that the layer including the water-soluble resin of the laminated film was laminated to the above-described fiber layer (B) composed of water-soluble polymer.

(3) Evaluation Results

The evaluation results for the PVA nonwoven fabric prepared in (1) above alone were as shown in Tables 1 and 2, and the evaluation results for the integrated sheet obtained using the PVA nonwoven fabric were as shown in Table 2. The PVA nonwoven fabric had almost no water resistance.

Comparative Example 4

(1) Spinning and a Calendering Treatment of the Fiber Layer (B) Composed of Water-Soluble Polymer The pullulan nonwoven fabric described in Example 1 was subjected to a calendering treatment with metal-metal rolls under the conditions of a temperature of 90° C., a linear pressure of 2 t/cm, a clearance of 0.23 mm, and a processing speed of 0.5 m/min.

(2) Preparation of an Integrated Sheet on which a Base Material (C) Composed of Sparingly Water-Soluble Polymer was Laminated An integrated sheet was prepared as in Example 1, except that the layer including the water-soluble resin of the laminated film was laminated to the above-described fiber layer (B) composed of water-soluble polymer.

(3) Evaluation Results

The evaluation results for the calendered pullulan nonwoven fabric prepared in (1) above alone were as shown in Tables 1 and 2, and the evaluation results for the integrated sheet obtained using the pullulan nonwoven fabric were as shown in Table 2. Although the pullulan nonwoven fabric had improved water resistance, it had a film-like texture, and was cracked when bent.

Comparative Example 5

(1) Spinning of a Fiber Layer (B) Composed of Water-Soluble Polymer

An aqueous solution of pullulan was spun using the ESP method as in Example 1, except that the distance between the nozzle tip and the collection electrode was 9 cm. The pullulan fibers spun using the ESP method were collected in the form of a nonwoven fabric, and an SEM observation thereof confirmed the formation of a film and a small amount of ultrafine fibers.

(2) Preparation of an Integrated Sheet on which a Base Material (C) Composed of Sparingly Water-Soluble Polymer was Laminated An integrated sheet was prepared as in Example 1, except that the layer including the water-soluble resin of the laminated film was laminated to the above-described fiber layer (B) composed of water-soluble polymer.

(3) Evaluation Results

The evaluation results for the pullulan nonwoven fabric prepared in (1) above alone were as shown in Tables 1 and 2, and the evaluation results for the integrated sheet obtained using the pullulan nonwoven fabric were as shown in Table 2. The pullulan nonwoven fabric had no water resistance, and had a hard texture. During the evaluation of the removability of the integrated sheet, the handleability was poor because pullulan became sticky due to water absorption.

Comparative Example 6

(1) Spinning of a Fiber Layer (B) Composed of Water-Soluble Polymer

A pullulan nonwoven fabric was produced as in Example 1.

(2) Spinning of a Layer (A) Composed of Sparingly Water-Soluble Polymer

To 73 mass parts of water, 22 mass parts of PVA having a degree of saponification of 99.1% (Japan Vam & Poval Co., Ltd.; product number: JF-05DH) was added while stirring at a room temperature of 20° C., and dissolved with stirring at a temperature of 95° C. The solution was slowly cooled to 20° C., thus giving an aqueous solution of PVA having a concentration of 22%.

As in Example 1, the aqueous solution of PVA was spun onto the pullulan nonwoven fabric sheet, using the ESP method. An 18-gauge (inner diameter: 0.94 mm) non-beveled needle was used as the nozzle, and a rotary roller having a diameter of 10 cm and a width of 30 cm to which a commercially available aluminum foil with a silicone was laminated was used as the collection electrode. The rotary roller was rotated at 50 cm/min, the discharge rate was 0.01 cm/min, the applied voltage was 28.0 kV, the traverse rate was 20 cm/min, the traverse width was 15 cm, and the distance between the nozzle tip and the collection electrode was 15 cm. The PVA fibers spun using the ESP method were collected in the form of a nonwoven fabric, and an SEM observation thereof confirmed formation of ultrafine fibers.

(3) Preparation of an Integrated Sheet on which a Base Material (C) Composed of Sparingly Water-Soluble Polymer was Laminated An integrated sheet was prepared as in Example 1.

(4) Evaluation Results

The evaluation results for the multilayer sheet were as shown in Tables 1 and 2, and the evaluation results for the integrated sheet were as shown in Table 2. Although the multilayer sheet was satisfactory in texture and surface quality, and the integrated sheet was also satisfactory in removability, the multilayer sheet had low water resistance.

TABLE 1

| | | Solute | Solute Concentration (%) | Nozzle Tip-to-Collection Electrode Distance (cm) | Basis Weight (g/m$^2$) | Fiber Diameter (μm) | Thickness (μm) | Form |
|---|---|---|---|---|---|---|---|---|
| Example 1 | A | PVA (n = 4000, h ≥ 99.0%) | 6 | 7 | 11 | Unmeasurable | 5.2 | Film and Small Amount of Ultrafine Fibers |
| | B | Pullulan | 20 | 15 | 127.5 | 0.387 | 340.0 | Ultrafine Fibers |
| Example 2 | A | PVA (n = 4000, h ≥ 99.0%) | 6 | 10 | 78.9 | Unmeasurable | 36.1 | Film and Ultrafine Fibers |
| | B | Pullulan | 20 | 15 | 127.5 | 0.387 | 340.0 | Ultrafine Fibers |
| Example 3 | A | PVA (n = 2000, h = 98.0~99.0%) | 10 | 7 | 19.5 | Unmeasurable | 11.1 | Film and Ultrafine Fibers |
| | B | Pullulan | 20 | 15 | 127.5 | 0.387 | 340.0 | Ultrafine Fibers |
| Example 4 | A | PVA (n = 1700, h = 95.5~97.5%) | 15 | 7 | 63 | Unmeasurable | 31.4 | Film and Ultrafine Fibers |
| | B | Pullulan | 20 | 15 | 127.5 | 0.387 | 340.0 | Ultrafine Fibers |
| Example 5 | A | PVA (n = 1300, h = 92.5~94.5%) | 20 | 7 | 124.6 | Unmeasurable | 45.2 | Film and Ultrafine Fibers |
| | B | Pullulan | 20 | 15 | 127.5 | 0.387 | 340.0 | Ultrafine Fibers |
| Example 6 | A | PVA (n = 4000, h ≥ 99.0%) | 6 | 7 | 11 | Unmeasurable | 5.2 | Film and Small Amount of Ultrafine Fibers |
| | B | PVA (n = 500, h = 86.5~89.0%) | 20 | 15 | 109.6 | 0.280 | 504.0 | Ultrafine Fibers |
| Example 7 | A | PVA (n = 1000, h = 98.0~99.0%) | 15 | 7 | 24.3 | Unmeasurable | 15.0 | Film and Ultrafine Fibers |
| | B | Pullulan | 20 | 15 | 127.5 | 0.387 | 340.0 | Ultrafine Fibers |
| Example 8 | A | PVA (n = 500, h = 99.1%) | 27 | 5.5 | 23.7 | Unmeasurable | 12.3 | Film and Ultrafine Fibers |
| | B | Pullulan | 20 | 15 | 127.5 | 0.387 | 340.0 | Ultrafine Fibers |
| Example 9 | A | PVA (n = 500, h = 99.1%) | 22 | 15 | 48.7 | 0.190 | 70.2 | Ultrafine Fibers |
| | B | Pullulan | 20 | 15 | 127.5 | 0.387 | 340.0 | Ultrafine Fibers |
| Comp. Ex. 1 | A | — | — | — | — | — | — | — |
| | B | Pullulan | 20 | 15 | 127.5 | 0.387 | 340.0 | Ultrafine Fibers |
| Comp. Ex. 2 | A | PVA (n = 4000, h ≥ 99.0%) | 6 | 7 | 11 | Unmeasurable | 5.2 | Film and Small Amount of Ultrafine Fibers |
| | B | — | — | — | — | — | — | — |
| Comp. Ex. 3 | A | — | — | — | — | — | — | — |
| | B | PVA (n = 500, h = 86.5~89.0%) | 20 | 15 | 109.6 | 0.280 | 504.0 | Ultrafine Fibers |
| Comp. Ex. 4 | A | — | — | — | — | — | — | — |
| | B | Pullulan | 20 | 15 | 127.5 | 0.584 | 200.0 | Ultrafine Fibers |
| Comp. Ex. 5 | A | — | — | — | — | — | — | — |
| | B | Pullulan | 20 | 9 | 5.1 | Unmeasurable | 5.0 | Film and Small Amount of Ultrafine Fibers |

TABLE 1-continued

|  |  | Solute | Solute Concentration (%) | Nozzle Tip-to-Collection Electrode Distance (cm) | Basis Weight (g/m²) | Fiber Diameter (μm) | Thickness (μm) | Form |
|---|---|---|---|---|---|---|---|---|
| Comp. Ex. 6 | A | PVA (n = 500, h = 99.1%) | 22 | 15 | 8.3 | 0.190 | 5.5 | Ultrafine Fibers |
|  | B | Pullulan | 20 | 15 | 127.5 | 0.387 | 340.0 | Ultrafine Fibers | n: Degree of Polymerization,
h: Degree of Saponification

TABLE 2

|  | Multilayer Sheet | | | | | Integrated |
|---|---|---|---|---|---|---|
|  | Water Resistance Evaluation (sec) | Surface Quality | Texture | Basis Weight (g/m²) | Tensile Strength (N/mm) | Sheet Removability Evaluation |
| Example 1 | 90 | Good | Good | 138.5 | 0.5 | Good |
| Example 2 | 12 | Good | Fair | 206.4 | 3.2 | Good |
| Example 3 | 60 | Good | Good | 147.0 | 1.1 | Good |
| Example 4 | 30 | Good | Good | 190.5 | 2.8 | Good |
| Example 5 | 20 | Good | Fair | 252.1 | 4.3 | Good |
| Example 6 | 90 | Good | Good | 120.6 | 0.6 | Good |
| Example 7 | 60 | Fair | Fair | 151.8 | 1.3 | Good |
| Example 8 | 30 | Fair | Fair | 151.2 | 1.1 | Good |
| Example 9 | 13 | Good | Fair | 176.2 | 0.5 | Good |
| Comp. Ex. 1 | 1 | Fair | Good | 127.5 | 0.1 | Good |
| Comp. Ex. 2 | 90 | Good | Poor | 11.0 | 0.4 | Poor |
| Comp. Ex. 3 | 1 | Fair | Good | 109.6 | 0.1 | Good |
| Comp. Ex. 4 | 20 | Fair | Poor | 127.5 | 0.2 | Fair |
| Comp. Ex. 5 | 0 | Good | Poor | 5.1 | 0.1 | Poor |
| Comp. Ex. 6 | 2 | Good | Good | 135.8 | 0.1 | Good |

Figure 6:
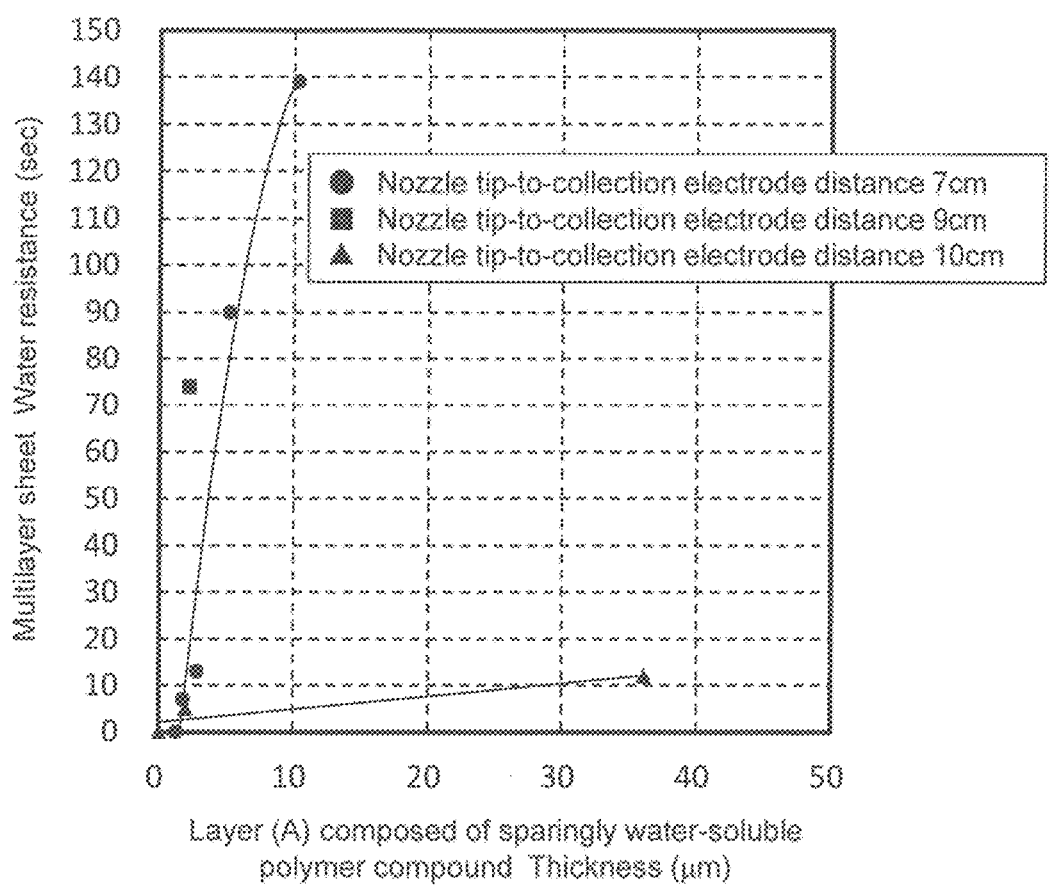
FIG. 6 shows a graph showing the relationship between the nozzle tip-to-collection electrode distance, the thickness of the layer (A) composed of sparingly water-soluble polymer, and the water resistance of the multilayer sheet, in the multilayer sheet.

3. Consideration of the Distance Between the Nozzle Tip and the Collection Electrode During Spinning of the Layer (A) Composed of Sparingly Water-Soluble Polymer The relationship between the nozzle tip-to-collection electrode distance, the thickness of the layer (A) composed of sparingly water-soluble polymer, and the water resistance of the multilayer sheet when an aqueous solution of PVA was spun onto a pullulan nonwoven fabric using the ESP method as in Example 1, was examined. The results are shown in the graph of FIG. 6. Note that the same PVA as that of Example 1 having a degree of saponification of 99.0% or more (Japan Vam & Poval Co., Ltd.; product number: JC-40) was used. When the distance between the nozzle tip and the collection electrode was reduced from 10 cm to 9 cm or less, it was observed that a predominant form of the layer (A) composed of sparingly water-soluble polymer changed from nanofibers into a film. As shown in the graph of FIG. 6, water resistance was remarkably improved by setting the distance between the nozzle tip and the collection electrode to 9 cm. It was therefore inferred that when the layer (A) composed of sparingly water-soluble polymer forms a film, high water resistance is expressed even with a small thickness.

All the publications, patents, and patent applications cited herein are incorporated by reference in their entirety herein.

The invention claimed is:

1. An integrated sheet comprising:
a multilayer sheet comprising:
one or more layers from each of
a non-fibrous layer (A) composed of a first sparingly water-soluble polymer having a thin-film structure having a defect or having an uneven thickness, and
a fiber layer (B) composed of water-soluble polymer are laminated, and
at least one of outermost layers is the layer (A) composed of the first sparingly water-soluble polymer, wherein
time taken from dropping of 0.04 mL water onto a surface of the layer (A) forming the outermost layer of the multilayer sheet composed of the first sparingly water-soluble polymer to dissolution of the other outermost layer of the multilayer sheet is 10 seconds to 5 minutes; and
a base material (C) composed of a second sparingly water-soluble polymer are integrally laminated,
wherein the non-fibrous layer (A) composed of the first sparingly water-soluble polymer forms one outermost layer of the integrated sheet, and the base material (C) composed of the second sparingly water-soluble polymer forms the other outermost layer of the integrated sheet,
the base material (C) is composed of polylactic acid, and
the compound forming the non-fibrous layer (A) composed of the first sparingly water-soluble polymer is a saponified polyvinyl alcohol having a degree of saponification of 92.5 to 100 mol %.

2. The integrated sheet according to claim 1, wherein a basis weight of the non-fibrous layer (A) composed of the first sparingly water-soluble polymer is 1 to 200 g/m².

3. The integrated sheet according to claim 1, wherein the multilayer sheet has a tensile strength of 0.1 to 5.0 N/mm.

4. The integrated sheet according to claim 1, wherein the non-fibrous layer (A) composed of the first sparingly water-soluble polymer is formed by collecting a fiber obtained by spinning a solution of the compound forming the layer using an electrospinning method, onto the fiber layer (B) composed of water-soluble polymer, and the spinning is performed by setting a distance between a nozzle tip that discharges the solution and a collection electrode of 3 to 10 cm.

* * * * *